(12) United States Patent
Vanhoorelbeke et al.

(10) Patent No.: US 11,339,226 B2
(45) Date of Patent: May 24, 2022

(54) HUMANISED ADAMTS13 BINDING ANTIBODIES

(71) Applicant: Katholieke Universiteit Leuven, Leuven (BE)

(72) Inventors: Karen Vanhoorelbeke, Zwevegem (BE); Shannen F. Deconinck, Avelgem (BE); An-Sofie Schelpe, Zwevegem (BE)

(73) Assignee: Katholieke Universiteit Leuven, Leuven (BE)

( * ) Notice: Subject to any disclaimer, the term of this patent is extended or adjusted under 35 U.S.C. 154(b) by 87 days.

(21) Appl. No.: 16/638,677

(22) PCT Filed: Jun. 13, 2018

(86) PCT No.: PCT/EP2018/065617
§ 371 (c)(1),
(2) Date: Feb. 12, 2020

(87) PCT Pub. No.: WO2018/229103
PCT Pub. Date: Dec. 20, 2018

(65) Prior Publication Data
US 2020/0308303 A1    Oct. 1, 2020

(30) Foreign Application Priority Data

Jun. 13, 2017 (GB) ...................................... 1709379

(51) Int. Cl.
*C07K 16/40* (2006.01)
*A61P 7/04* (2006.01)
*A61K 39/00* (2006.01)

(52) U.S. Cl.
CPC ............... *C07K 16/40* (2013.01); *A61P 7/04* (2018.01); *A61K 2039/505* (2013.01); *C07K 2317/24* (2013.01); *C07K 2317/33* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 6/1998 | Wigler et al. |
| 5,821,047 A | 10/1998 | Garrad et al. |
| 5,969,108 A | 10/1999 | McCafferty et al. |
| 6,180,370 B1 * | 1/2001 | Queen ................ C07K 16/2866 435/69.6 |
| 10,829,562 B2 * | 11/2020 | Vanhoorelbeke .. A61K 39/3955 |

FOREIGN PATENT DOCUMENTS

| | | |
|---|---|---|
| WO | 9201047 A1 | 1/1992 |
| WO | 9218619 A1 | 10/1992 |
| WO | 9222324 A1 | 12/1992 |
| WO | 93011236 A1 | 6/1993 |
| WO | 9404678 A1 | 3/1994 |
| WO | 9515982 A2 | 6/1995 |
| WO | 9520401 A1 | 8/1995 |
| WO | 199749805 A2 | 12/1997 |
| WO | 2009110737 A2 | 9/2009 |
| WO | 2015158851 A1 | 10/2015 |
| WO | 2017097889 A1 | 6/2017 |

OTHER PUBLICATIONS

Sela-Culang, Inbal, Vered Kunik, and Yanay Ofran. "The structural basis of antibody-antigen recognition." Frontiers in immunology 4 (2013): 302 (Year: 2013).*
Xiang, Jim, et al. "Framework residues 71 and 93 of the chimeric B72. 3 antibody are major determinants of the conformation of heavy-chain hypervariable loops." (1995): 385-390. (Year: 1995).*
Colman, Peter M. "Effects of amino acid sequence changes on antibody-antigen interactions." Research in Immunology 145.1 (1994): 33-36. (Year: 1994).*
Lubert Stryer, Biochemistry, 4th, WH Freeman, New York (1995) ISBN: 0-7167-2009-4 (Year: 1995).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Presta, et al., "Antibody engineering", Current Opinion in Structural Biology, vol. 2, pp. 593-596, 1992.
International Search Report in reference to co-pending European Patent Application No. PCT/EP2018/06517 filed Jun. 13, 2018.
Almagro, et al., "Humanization of antibodies", Frontiers of Bioscience, vol. 13, pp. 1619-1633, Jan. 1, 2008.
Ames, et al., "Conversion of murine Fabs isolated from combinatorial phage display library to full length Immunoglobulins", Journal of Immunological Methods, vol. 184, pp. 177-186, 1995.
Better, et al., "*Escherichia coli* Secretion of an Active Chimeric Antibody Fragment", Science, pp. 1041-1043, May 20, 1988.

(Continued)

*Primary Examiner* — Michael Szperka
*Assistant Examiner* — Lia E Taylor
(74) *Attorney, Agent, or Firm* — Dinsmore & Shohl, LLP

(57) ABSTRACT

The present invention further relates to specific humanised monoclonal antibodies inhibiting ADAMTS13 function. The present invention relates to methods of treatment by human ADAMTS13 inhibition in circulatory assist device induced haemorrhagic complication such as a bleeding disorder, in particular, bleeding after left ventricular assist device (LVAD) implantation.

7 Claims, 16 Drawing Sheets
Specification includes a Sequence Listing.

(56) References Cited

OTHER PUBLICATIONS

Boder, et al., "Directed evolution of antibody fragments with monovalent femtomolar antigen-binding affinity", Applied Biological Sciences, vol. 97, No. 20, Sep. 26, 2000.
Borras, et al., "Generic Approach for the Generation of Stable Humanized Single-chain Fv Fragments from Rabbit Monoclonal Antibodies", The Journal of Biological Chemistry, vol. 285, No. 12, pp. 9054-9066, Mar. 19, 2010.
Brinkmann, et al., Phage display of disulfide-stabilized Fv fragments, Journal of Immunological Methods, vol. 182, pp. 41-50, 1995.
Burton, et al., "Human Antibodies from Combinatorial Libraries", Advances in Immunology, vol. 57, pp. 191-280, 1994.
Carter, et al., "High Level *Escherichia coli* Expression and Production of a Bivalent Humanized Antibody Fragment", Bio/Technology, vol. 10, pp. 163-167, Feb. 1992.
Davies, et al., "Affinity improvement of single antibody VH domains: residues in all three hypervariable regions affect antigen binding", Immunotechnology, vol. 2, pp. 169-179, 1996.
De Ceunynck, et al., "Local Elongation of Endothelial Cell-anchored von Willebrand Factor Strings Precedes ADAMTS13 Protein-mediated Proteolysis", The Journal of Biological Chemistry, vol. 286, No. 42, pp. 36361-36367, Oct. 21, 2011.
De Pascalis, et al., "Grafting of (Abbreviated) Complimentarity-Determining Regions Containing Specificity-Determining Residues Essential for Ligand Contact to Engineer a Less Immunogenic Humanized Monoclonal Antibody", The Journal of Immunology, pp. 3076-3084, 2002.
Deforche, et al., "Linker regions and flexibility around the metalloprotease domain account for conformational activation of ADAMTS-13", Journal of Thrombosis and Haemostasis, vol. 12, pp. 2063-2075, 2015.
Feys, et al., "Thrombotic Thrombocytopenic purpura directly linked with ADAMTS13 inhibition in the baboon (*Papio ursinus*)". Plenary Paper, vol. 116, No. 12, pp. 2005-2010, Sep. 23, 2010.
Furukawa, et al., "A Role of the Third Complimentarity-determining Region in the Affinity Maturation of an Antibody", The Journal of Biological Chemistry, vol. 276, No. 29, pp. 27622-27628, 2001.
Gram, et al., "In vitro selection and affinity maturation of antibodies from a naive combinatorial immunoglobulin library", Proc. Natl. Acad Sci., vol. 89, pp. 3576-3580, Apr. 1992.
Harding, et al., The immunogenicity of humanized and fully human antibodies, Landes Bioscience, vol. 2, Issue 3, pp. 256-265, 2010.
Huston, et al., "Protein Engineering of Single-Chain Fv Analogs and Fusion Proteins", Antibodies and Antigens, vol. 203, pp. 46-89, 1999.
Huston, et al., "Protein engineering of antibody binding sites: Recovery of specific activity in an anti-digoxin single-chain Fv analogue produced in *Escherichia coli*", Proc. Natl. Acad. Sci., Biochemistry, vol. 85, pp. 5879-5883, Aug. 1988.
Jones, et al., "Replacing the complementarity-determining regions in a human antibody with those form a mouse", Nature Publishing Group, vol. 321, pp. 522-525, May 1986.
Kashmiri, et al., "SDR grafting—a new approach to antibody humanization", Science Direct, Elsevier, vol. 36, pp. 25-34, 2005.
Kettleborough, et al., "Isolation of tumor cell-specific single-chain Fv from immunized mice using phage-antibody libraries and the re-construction of whole antibodies from these antibody fragments", European Journal Immunol., vol. 24, pp. 952-952, 1994.
Lefranc, et al., "IMGT®, the international ImMunoGeneTics information system® 25 years on", Nucleic Acids Research, vol. 43, pp. D413-D4122, 2015.
Muia, et al., "An optimized fluorogenic ADAMTS13 assay with increased sensitivity for the investigation of patients with thrombotic thrombocytopenic purpura", Journal of Thrombosis and Haemostasis, pp. 1511-1518, 2013.

Mullinax, et al., "Expression of a Heterodimeric Fab Antibody Protein in One Cloning Step", Research Report, vol. 12, No. 6, pp. 864-867, 1992.
Melson, "Antibody fragments", Point of View, Landes Bioscience, vol. 2, Issue 1, pages 77-83, 2010.
Ostertag, et al., "ADAMTS13 Autoantibodies Cloned from Patients with Acquire Thrombotic Thrombocytopenic Purpura: 1. Structural and functional characterization in vitro", HHS Public Access, Author Manuscript, pp. 1763-1774, Jul. 2016.
Ostertag, et al., "ADAMTS13 Autoantibodies Cloned from Patients with Acquire Thrombotic Thrombocytopenic Purpura: 2. Pathogenicity in an animal model", HHS Public Access, Author Manuscript, pp. 1775-1785, Jul. 2016.
Padlan, et al., "Identification of specificity-determining residues in antibodies", Research Communications, pp. 133-139, 1995.
Persic, et al., "An integrated vector system for the eukaryotic expression of antibodies or their fragments after selection from phage display libraries", GENE An International Journal Genes and Genomes, pp. 9-18, 1997.
Plückthun, "Antibodies from *Escherichia coli*", Chapter 11, pp. 269-315, 1994.
Pos, et al., "An autoantibody epitope comprising residues R660, Y661, and Y665 in the ADAMTS13 spacer domain identifies a binding site for the A2 domain of VWF", Thrombosis and Hemostasis, vol. 115, No. 8, pp. 1640-1649, Feb. 2010.
Plückthun, "Antibody engineering", Current in Opinion in Biotechnology, pp. 238-246, 1991.
Rader, et al., "A Phage display approach for rapid antibody humanization: Designed combinatorial V gene libraries", Proc. Natl. Acad. Sci., vol. 95, pp. 8910-8915, Jul. 1998.
Rauch, et al., "Antibody-based prevention of von Willebrand factor degradation mediated by circulatory assist devices", Cardiovascular Biology and Cell Signalling, pp. 1014-1023, 2014.
Reichmann, et al., "Reshaping human antibodies for therapy", Nature, vol. 332, pp. 323-327, Mar. 24, 1988.
Sawai, et al., "Direct Production of the Fab Fragment Derived From the Sperm Immobilizing Antibody Using Polymerase Chain Reaction and cDNA Expression Vectors", American Journal of Reproductive Immunology, vol. 34, pp. 27-34, 1995.
Schaffer, et al., "Bleeding Complications and Blood Product Utilization With Left Ventricular Assist Device Implantation", The Society of Thoracic Surgeons, pp. 740-749, 2011.
Short, et al., "Complementary Combining Site Contact Residue Mutations of the Anti-dioxin Fab 26-10 Permit High Affinity Wild-type Binding", The Journal of Biological Chemistry, vol. 277, No. 19, pp. 16365-16370, 2002.
Shu, et al., "Secretion of a single-gene-encoded immunoglobulin from myeloma cells", Proc. Natl. Acad. Sci., vol. 90, pp. 7995-7999, Sep. 1993.
Skerra, et al., "Assembly of a Functional Immunoglobulin Fv Fragment in *Escherichia coli*", Science, pp. 1038-1041, May 20, 1988.
Thompson, et al., "Affinity Maturation of a High-affinity Human Monoclonal Antibody Against the Third Hypervariable Loop of Human Immunodeficiency Virus: Use of Phage Display to Improve Affinity and Broaden Strain Reactivity", Journal of Molecular Biology, vol. 256, pp. 77-88, 1996.
Vanhoorelbeke, et al., "A Reliable and Reproducible ELISA Method to Measure Ristocetin Cofactor Activity of von Willebrand Factor", Download from Katholieke Universiteit Leuven, pp. 107-113, 2000.
Vaughan, et al., "Human Antibodies by design", Nature Biotechnology, vol. 16, pp. 535-539, Jun. 1998.
Vincke, et al., "General Strategy to Humanize a Camelid Single-domain Antibody and Identification of a Universal Humanized Nanobody Scaffold", The Journal of Biological Chemistry, vol. 284, No. 5, pp. 3273-3284, Jan. 30, 2009.
European Search Report in reference to co-pending European Patent Application No. 0239400 filed Mar. 26, 1987.
Ye, et al., "IgBLAST: an immunoglobulin variable domain sequence analysis tool", Nucleic Acids Research, vol. 41, pp. W34-W40, May 13, 2013.

(56) References Cited

OTHER PUBLICATIONS

Yang, et al., CDR Walking Mutagenesis for the Affinity Maturation of a Potent Human Anti-HIV-1 Antibody into the Picomolar Range, Journal of Molecular Biology, vol. 254, pp. 392-403, 1995.
Written Opinion in reference to co-pending European Patent Application No. PCT/EP2018/065617 filed Jun. 13, 2018.

* cited by examiner

E
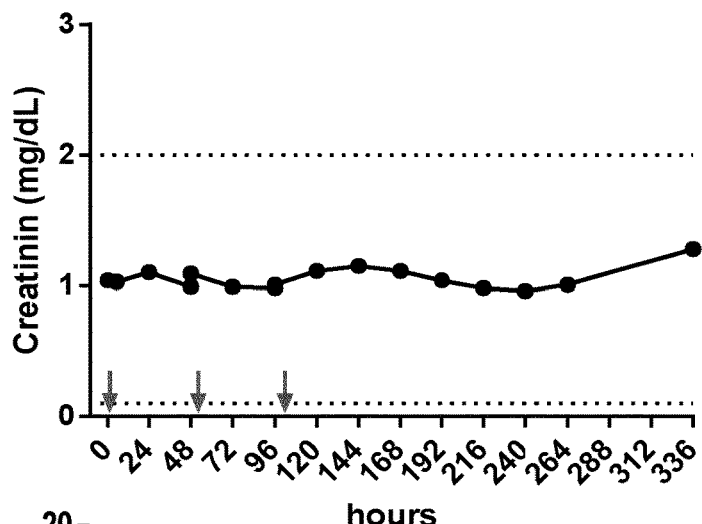
F
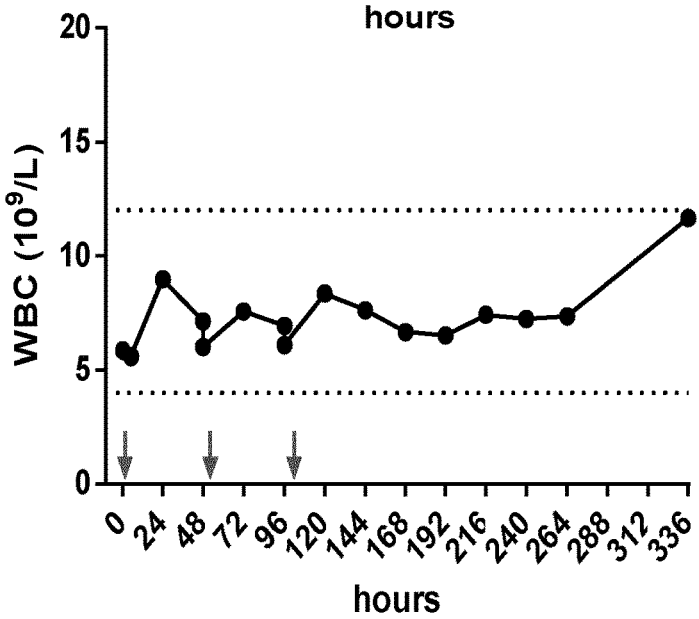
G
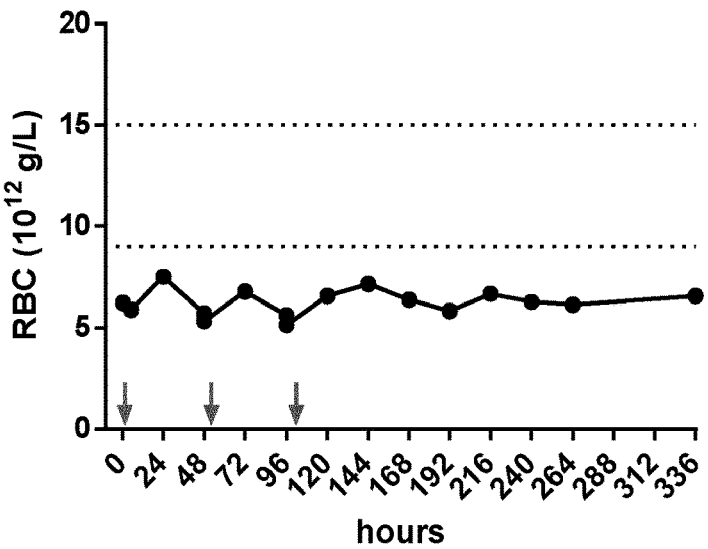
Figure 13 (continued)

```
humanized sequences of 17C7 antibody VH
based on IMGT IGHV3-21*01 acceptor framework seq              10         20         30         40         50
AbM              10         20         30         40         50      a
             b b b      p    b b b b    b b    b bi i     i ibb b
17C7         EVQLVESGGDLVKSGGSLKLSCAAS GFIFSNYAMS WVRQTPEKRLEWGA TITTGGFYTF  [SEQ ID NO:1]
                 *                          *                  *  *
IGHV3-21*01  EVQLVESGGGLVKPGGSLRLSCAAS GFTFSSYSMN WVRQAPGKGLEWVS SISSSSSYIY [SEQ ID NO:2]
hMAB2-H1     EVQLVESGGGLVKPGGSLRLSCAAS GFIFSNYAMS WVRQAPGKGLEWVS TITTGGFYTF [SEQ ID NO:3]
hMAB2-H2     EVQLVESGGGLVKPGGSLRLSCAAS GFIFSNYAMS WVRQAPGKGLEWGA TITTGGFYTF [SEQ ID NO:4]
                                           # seq         60         70        80         90         100        110         120
AbM         60         70        80  abc        90                110
            i    b   b b b x    b b b  b        bibibb    bibibb            i    b b b
17C7        YSDSVKGRFTISRDNAKNTLYLQMSSLRSEDTAMYYCAR HRYDDYYALDY WGQGTLVTVSS [SEQ ID NO:1]
                *                    *     *      *
IGHV3-21*01 YADSVKGRFTISRDNAKNSLYLQMNSLRAEDTAVYYCAR                          WGQGTLVTVSS [SEQ ID NO:2]
            S                                           M
hMAB2-H1    YADSVKGRFTISRDNAKNSLYLQMNSLRAEDTAVYYCAR HRYDDYYALDY WGQGTLVTVSS [SEQ ID NO:3]
hMAB2-H2    YADSVKGRFTISRDNAKNSLYLQMNSLRAEDTAVYYCAR HRYDDYYALDY WGQGTLVTVSS [SEQ ID NO:4]

# Asn deamidation substitutions: Q/S/A/D
```

Figure 14 humanized sequences of 17C7 antibody VL
based on IMGT IGKV3-11*01 acceptor framework (AbM CDR definition)

```
seq             10         20         30         40         50
AbM             10         20      30 34         40         50
          b b b       p p     b b b   b b bi   bi i ii ibbi   i
17C7      ENVLTQSPAIMSTSPGEKVTMTC NVSSSVSYMR WFQQKSSTSPKLWIY DTSKLAS   [SEQ ID NO:5]
             *                    **  **                 *

3-11*01   EIVLTQSPATLSLSPGERATLSC RASQSVSSYLA WYQQKPGQAPRLLIY DASNRAT
hMAB2-L1  EIVLTQSPATLSLSPGERATLSC NVSSSVSYMR  WYQQKPGQAPRLLIY DTSKLAS  [SEQ ID NO:6]
hMAB2-L2  EIVLTQSPATLSLSPGERATLSC NVSSSVSYMR  WFQQKPGQAPRLWIY DTSKLAS  [SEQ ID NO:7]
hMAB2-L3  EIVLTQSPATLSLSPGERVTMSC NVSSSVSYMR  WFQQKPGQAPRLWIY DTSKLAS  [SEQ ID NO:8]
hMAB2-L5a EIVLTQSPATLSLSPGERVTMSC RVSSSVSYMR  WFQQKPGQAPRLWIY DTSKLAS  [SEQ ID NO:9]
hMAB2-L4  EIVLTQSPATMSTSPGERVTMSC NVSSSVSYMR  WFQQKPGQAPRLWIY DTSKLAS  [SEQ ID NO:10]
hMAB2-L5b EIVLTQSPATMSTSPGERVTMSC RVSSSVSYMR  WFQQKPGQAPRLWIY DTSKLAS  [SEQ ID NO:11]
                                      #                              [SEQ ID NO:12]
           N                                           S seq             60         70         80         90        100
AbM             60         70         80         90        100
           b        b          b b b b   ib bib   ibi iib   i  b b b
17C7       GVPGRFSGSGSGHSYSLTISSMEADDVATYYC FQGNGYPLT FGAGTKLELK       [SEQ ID NO:5]
              *                    ** * *                *

3-11*01    GIPARFSGSGSGTDFTLTISSLEPEDFAVYYC QQRSNWPP
hMAB2-L1   GIPARFSGSGSGTDFTLTISSLEPEDFAVYYC FQGNGYPLT FGQGTKLEIK        [SEQ ID NO:6]
hMAB2-L2   GIPARFSGSGSGTDFTLTISSLEPEDFAVYYC FQGNGYPLT FGQGTKLEIK        [SEQ ID NO:7]
hMAB2-L3   GVPARFSGSGSGTDYTLTISSMEPEDFAVYYC FQGNGYPLT FGQGTKLEIK        [SEQ ID NO:8]
hMAB2-L5a  GVPARFSGSGSGTDYTLTISSMEPEDFAVYYC FQGNGYPLT FGQGTKLEIK        [SEQ ID NO:9]
hMAB2-L4   GVPARFSGSGSGTDYTLTISSMEPEDFAVYYC FQGNGYPLT FGQGTKLEIK        [SEQ ID NO:10]
hMAB2-L5b  GVPARFSGSGSGTDYTLTISSMEPEDFAVYYC FQGNGYPLT FGQGTKLEIK        [SEQ ID NO:11]
                                                                      [SEQ ID NO:12]
                         V                @                I
```

Figure 14 (continued)

Variable heavy chain sequence fragments

```
Framework 1 sequences
17C7         EVQLVESGGDLVKSGGSLKLSCAAS  [SEQ ID NO:13]
hMAB2-H1     EVQLVESGGGLVKPGGSLRLSCAAS  [SEQ ID NO:14]
hMAB2-H2     EVQLVESGGGLVKPGGSLRLSCAAS  [SEQ ID NO:14]

VH CDR1 sequences
Consensus  GFIFS&YAMS  & = NQSAD    [SEQ ID NO:15]
17C7       GFIFSNYAMS               [SEQ ID NO:16]
hMAB2-H1   GFIFSNYAMS               [SEQ ID NO:16]
hMAB2-H2   GFIFSNYAMS               [SEQ ID NO:16]

Framework 2 sequences
Consensus   WVRQAPGKGLEWVS     [SEQ ID NO:17]
                        GA
17C7        WVRQTPEKRLEWGA     [SEQ ID NO:18]
hMAB2-H1    WVRQAPGKGLEWVS     [SEQ ID NO:19]
hMAB2-H2    WVRQAPGKGLEWGA     [SEQ ID NO:20]

VH CDR2 sequences
17C7        TITTGGFYTF  [SEQ ID NO:21]
hMAB2-H1    TITTGGFYTF  [SEQ ID NO:21]
hMAB2-H2    TITTGGFYTF  [SEQ ID NO:21]

Framework 3 sequences
Cons.    YADSVKGRFTISRDNAKNSLYLQMNSLRAEDTAMYYCAR[SEQ ID NO:22]
             S                                V
17C7     YSDSVKGRFTISRDNAKNTLYLQMSSLRSEDTAMYYCAR[SEQ ID NO:23]
hMAB2H1  YADSVKGRFTISRDNAKNSLYLQMNSLRAEDTAVYYCAR[SEQ ID NO:24]
hMAB2H2  YADSVKGRFTISRDNAKNSLYLQMNSLRAEDTAVYYCAR[SEQ ID NO:24]

VH CDR3 sequences
17C7        HRYDDYYALDY  [SEQ ID NO:25]
hMAB2-H1    HRYDDYYALDY  [SEQ ID NO:25]
hMAB2-H2    HRYDDYYALDY  [SEQ ID NO:25]

VH framework 4
17C7        WGQGTSVTVSS[SEQ ID NO:26]
hMAB2-H1    WGQGTLVTVSS[SEQ ID NO:27]
hMAB2-H2    WGQGTLVTVSS[SEQ ID NO:27]
```

Figure 14 (continued)

Variable light chain fragments

```
Framework 1 sequences
Consensus    EIVLTQSPATLSLSPGERATLSC        [SEQ ID NO:28]
                N      M T      V M
17C7         ENVLTQSPAIMSTSPGEKVTMTC        [SEQ ID NO:29]
hMAB2-L1     EIVLTQSPATLSLSPGERATLSC        [SEQ ID NO:30]
hMAB2-L2     EIVLTQSPATLSLSPGERATLSC        [SEQ ID NO:30]
hMAB2-L3     EIVLTQSPATLSLSPGERVTMSC        [SEQ ID NO:31]
hMAB2-L5a    EIVLTQSPATLSLSPGERVTMSC        [SEQ ID NO:31]
hMAB2-L4     EIVLTQSPATMSTSPGERVTMSC        [SEQ ID NO:32]
hMAB2-L5b    EIVLTQSPATMSTSPGERVTMSC        [SEQ ID NO:32]

VL CDR1
Consensus    &VSSSVSYMR    &= RNQSAD    [SEQ ID NO:33]
17C7         NVSSSVSYMR              [SEQ ID NO:34]
hMAB2-L1     NVSSSVSYMR              [SEQ ID NO:34]
hMAB2-L2     NVSSSVSYMR              [SEQ ID NO:34]
hMAB2-L3     NVSSSVSYMR              [SEQ ID NO:34]
hMAB2-L5a    RVSSSVSYMR              [SEQ ID NO:35]
hMAB2-L4     NVSSSVSYMR              [SEQ ID NO:34]
hMAB2-L5b    RVSSSVSYMR              [SEQ ID NO:35]

VL Framework 2
consensus    WYQQKPGQAPRLLIY        [SEQ ID NO:36]
              F       S  W
17C7         WFQQKSSTSPKLWIY        [SEQ ID NO:37]
hMAB2-L1     WYQQKPGQAPRLLIY        [SEQ ID NO:38]
hMAB2-L2     WFQQKPGQAPRLWIY        [SEQ ID NO:39]
hMAB2-L3     WFQQKPGQAPRLWIY        [SEQ ID NO:39]
hMAB2-L5a    WFQQKPGQAPRLWIY        [SEQ ID NO:39]
hMAB2-L4     WFQQKPGQAPRLWIY        [SEQ ID NO:39]
hMAB2-L5b    WFQQKPGQAPRLWIY        [SEQ ID NO:39]

VL CDR2
17C7              DTSKLAS    [SEQ ID NO:40]
hMAB2-L1          DTSKLAS    [SEQ ID NO:40]
hMAB2-L2          DTSKLAS    [SEQ ID NO:40]
hMAB2-L3          DTSKLAS    [SEQ ID NO:40]
hMAB2-L5a         DTSKLAS    [SEQ ID NO:40]
hMAB2-L4          DTSKLAS    [SEQ ID NO:40]
hMAB2-L5b         DTSKLAS    [SEQ ID NO:40]
```

Figure 14 (continued)

```
VL framework 3
Consensus   GIPARFSGSGSGTDYTLTISSLEPEDFAVYYC [SEQ ID NO:41]
              V            F   M    V
17C7        GVPGRFSGSGSGHSYSLTISSMEADDVATYYC [SEQ ID NO:42]
hMAB2-L1    GIPARFSGSGSGTDFTLTISSLEPEDFAVYYC [SEQ ID NO:43]
hMAB2-L2    GIPARFSGSGSGTDYTLTISSLEPEDFAVYYC [SEQ ID NO:44]
hMAB2-L3    GVPARFSGSGSGTDYTLTISSMEPEDFAVYYC [SEQ ID NO:45]
hMAB2-L5a   GVPARFSGSGSGTDYTLTISSMEPEDFAVYYC [SEQ ID NO:45]
hMAB2-L4    GVPARFSGSGSGTDYTLTISSMEPEDFAVYYC [SEQ ID NO:45]
hMAB2-L5b   GVPARFSGSGSGTDYTLTISSMEPEDFAVYYC [SEQ ID NO:46]

VL CDR 3 sequences
Consensus    FQG&GYPLT  &= NQSA [SEQ ID NO:47]
17C7         FQGNGYPLT         [SEQ ID NO:48]
hMAB2-L1     FQGNGYPLT         [SEQ ID NO:48]
hMAB2-L2     FQGNGYPLT         [SEQ ID NO:48]
hMAB2-L3     FQGNGYPLT         [SEQ ID NO:48]
hMAB2-L5a    FQGNGYPLT         [SEQ ID NO:48]
hMAB2-L4     FQGNGYPLT         [SEQ ID NO:48]
hMAB2-L5b    FQGNGYPLT         [SEQ ID NO:48]

VL framework 4
Consensus    FGQGTKLEIK    [SEQ ID NO:49]
                    L
17C7         FGAGTKLELK    [SEQ ID NO:50]
hMAB2-L1     FGQGTKLEIK    [SEQ ID NO:51]
hMAB2-L2     FGQGTKLEIK    [SEQ ID NO:51]
hMAB2-L3     FGQGTKLEIK    [SEQ ID NO:51]
hMAB2-L5a    FGQGTKLEIK    [SEQ ID NO:51]
hMAB2-L4     FGQGTKLEIK    [SEQ ID NO:51]
hMAB2-L5b    FGQGTKLEIK    [SEQ ID NO:51]
```

Figure 14 (continued)

HUMANISED ADAMTS13 BINDING ANTIBODIES

FIELD OF THE INVENTION

The present invention relates to treatments of haemorrhagic complications such as bleeding disorders due to a circulatory assist device implant.

The present invention further relates to humanised monoclonal antibodies which selectively bind to ADAMTS13 and inhibit its enzymatic activity.

BACKGROUND OF THE INVENTION

Human ADAMTS13 (A Disintegrin And Metalloproteinase with a ThromboSpondin type 1 motif, member 13), is a zinc-containing metalloprotease enzyme that cleaves von human von Willebrand factor (VWF).

An anti-ADAMTS13 monoclonal antibody 3H9 has been described [Feys et al. (2010) *Blood* 116, 2005-2010]. mAb 3H9 binds an epitope in the metalloprotease domain of ADAMTS13, and has been shown to inhibit the human ADAMTS13 and to cross-inhibit ADAMTS13 in baboon plasma. The antibody induced thrombotic thrombocytopenic purpura (TTP) in baboons at two boluses of 600 μg/kg administered intravenously to baboons at 0 h and 48 h, showing that ADAMTS13 function is essential for maintaining microvascular integrity in nonhuman primates. The anti-ADAMTS13 monoclonal antibody 3H9 has also been shown to inhibit the ADAMTS13 mediated proteolysis of VWF strings, which are UL-VWF multimers decorated with platelets persisting on the endothelial surface both in vitro and in vivo for several minutes (De Ceunynck et al. (2011) *J Biol Chem* 286: 36361-36367), as well as the ADAMTS13 mediated proteolysis of the VWF peptide VWF73 (Deforche et al. (2015) *J Thromb Haemost.* 13, 2063-2075).

In the above studies, ADAMTS13 inhibition has been studied in its relation to thrombotic thrombocytopenic purpura. Linking ADAMTS13 inhibition using 3H9 with treatment of aVWS was not reported.

Continuous-flow left ventricular assist devices (CF-LVADs) have become the standard of care for patients with end-stage heart failure (HF). However, haemorrhagic episodes in patients carrying implanted circulatory assist devices represent a severe life-threatening clinical complication, which is currently the leading complication in patients undergoing left ventricular assist device (LVAD) support. Such bleeding complications are a major source of morbidity and reoperation after left ventricular assist device (LVAD) implantation, yet remain poorly characterized in patients receiving LVADs (Schaffer J M (2011) *Ann Thorac Surg.* 91, 740-747, 747-749).

WO2016164468 and corresponding publications [Ostertag (2016) Transfusion. 56, 1775-1785; Ostertag et al. (2016) Transfusion. 56 1763-1774 disclose human anti-ADAMTS13 autoantibodies from immune-mediated TTP patients. These Ab bind to the (cysteine-) spacer domain and inhibit ADAMTS13 function in vitro under static conditions. Inhibition is obtained by binding to an exosite in the ADAMTS13 spacer domain that is involved in binding to VWF. Under shear conditions this type of antibody only partially inhibited ADAMTS13 activity (Pos et al. (2010) Blood 115, 1640-1649).

WO2015158851 discloses antibodies which bind to the D4 domain of VWF, competes for binding to VWF D4 domain with ADAMTS13 and partially inhibits ADAMTS13-mediated degradation of VWF.

Rauch et al. (2014) *Thromb Haemost.* 112, 1014-1023 disclose the partial (about) inhibition of VWF-ADAMTS13 interactions using an anti-VWF antibody to prevent VWF degradation mediated by circulatory assist devices. However, in this approach the size of the vWF complex is increased, parts of vWF are shielded from interactions other than with ADAMTS13.

Alternative strategies targeting the other partner in the VWF-ADAMTS13 have not been investigated.

PCT/EP2016/080229 filed on Dec. 8, 2016, and published on Jun. 15, 2017 as WO2017097889 discloses murine monoclonal antibodies 3H9 and 17c7 against ADAMTS13.

SUMMARY OF THE INVENTION

One aspect of the invention relates to humanised monoclonal antibodies specifically binding to ADAMTS13 and inhibiting VWF cleavage by ADAMTS13 for use in the treatment or prevention of a haemorrhagic complication or bleeding disorder in a subject carrying an implanted circulatory assist device.

Further, the methods and compounds of the present invention can be used to treat or prevent haemorrhagic complications or bleeding disorders caused by high shear stress in patients without implanted LVAD like patients suffering from Heyde's syndrome and patients with a veno-venous Extra Corporeal Membrane Oxygenation support (ECMO) for respiratory support.

The antigen binding molecules of the invention are humanised monoclonal antibodies or antigen binding fragments thereof.

The antigen binding molecule can be aFab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody.

A specific embodiment of the antigen binding molecule is a fragment of a monoclonal antibody of the group consisting of a scFV, Fab, Fab2, F(ab')2, Fv or dAb.

The present invention relates to methods of treatment by human ADAMTS13 inhibition, in a subject in need thereof, of haemorrhagic complications such as bleeding disorders due to a circulatory assist device implant. In particular it concerns to treat or prevent bleeding after left ventricular assist device (LVAD) implantation in heart patients by a selective inhibition of human ADAMTS13. The invention also provides antibodies, compositions and methods for preventing and/or treating such bleeding disorders in a subject carrying an implanted circulatory assist device or for preventing and/or treating such bleeding disorders caused by an implanted circulatory assist device using said antibodies, compositions or methods.

The present invention also relates to humanised monoclonal antibodies, and antigen binding fragments thereof, against human ADAMTS13 protein suitable for the purposes of the present invention and it provides furthermore nucleic acids encoding such antibodies and antibody fragments, cell lines producing such antibodies and antibody fragments, and antibody compositions against human ADAMTS13.

Antibodies of the present invention can be used in a dose dependent range to obtain partial up to complete inhibition of ADAMTS13.

Inhibition of ADAMTS13 has the advantage in that, apart from VWF cleavage, no other functions of vWF are influenced. The antibodies do not bind to VWF and have thus no effect on the size of vWF complexes. The antibodies neither shield certain domains of VWF whereby other interactions with vWF are inhibited.

The AB disclosed in WO20161611118, WO2016164468 will only partially inhibit ADAMTS13 function under shear conditions, for example in patients with an assist device implanted (an LVAD or Impella pump). The antibodies of the present invention targets the active site in ADAMTS13 and fully inhibit ADAMTS13 activity under shear conditions in an in vitro assist device (Impella pump) and have improved properties over anti-spacer antibodies such as disclosed in WO2016164468.

Compared to antibodies against vWF, inhibiting antibodies against ADAMTS13 as disclosed in the present invention can be used at concentrations which block ADAMTS13 without detrimental side effects. Indeed, blood parameters are normal upon use of the antibody.

The use of antibodies against ADAMTS13 has further additional advantages compared to vWF binding antibodies. vWF is the only substrate of ADAMTS13. By inhibiting ADAMTS13 only vWF cleavage is inhibited.

Circulatory assist devices generate shear stress which has an effect on vWF multimer formation. Anti-vWF antibodies not only have an effect on ADAMTS13 cleavage but also by binding increase the size of vWF complexes, resulting in an additional level of complexity which is not encountered with ADAMTS13 antibodies.

The invention is further summarised in the following statements:

1. A humanised antibody, specifically binding to ADAMTS13 and inhibiting VWF cleavage by ADAMTS13, or an antigen binding fragment of said antibody comprising:
   a variable heavy (VH) chain comprising:
      a Framework 1 having the sequence EVQLVESGG-GLVKPGGSLRLSCAAS [SEQ ID NO: 14],
      a CDR1 region having the sequence GFIFS[NQSAD]YAMS [SEQ ID NO:15],
      a Framework 2 having the sequence WVRQAPGK-GLEW[VG][SA] [SEQ ID NO:17],
      a CDR2 region having the sequence TITTGGFYTF [SEQ ID NO:21],
      a Framework 3 having the sequence Y[AS]DSVKGRFTISRDNAKNSLYLQMNSLRAE-DTA[VM]YYCAR [SEQ ID NO:22],
      a CDR3 region having the sequence HRYDDYYALDY [SEQ ID NO:25], and
      a Framework 4 having the sequence WGQGTLVTVSS [SEQ ID NO:27], and
   a variable light (VL) chain comprising:
      a framework 1 having the sequence E[I]VLTQSPAT[LM]S[LT]SPGER[AV]T[LM]SC [SEQ ID NO:28],
      a CDR1 region having the sequence [RNQSAD]VSSSVSYMR [SEQ ID NO:33],
      a framework 2 having the sequence W[YF]QQKPGQ[AS]PRL[LW]IY [SEQ ID NO:36],
      a CDR2 region having the sequence DTSKLAS [SEQ ID NO:40],
      a framework 3 having the sequence G[IV]PARFSGSGSGTD[FY]TLTISS[LM]EPED[FV]AVYYC [SEQ ID NO:41],
      a CDR3 region having the sequence FQG[NQSA]GYPLT [SEQ ID NO:47], and
      a Framework 4 having the sequence FGQGTKLE[IL]K [SEQ ID NO:49], or a sequence having up to 10 modified amino acids outside the CDR regions in the framework sequences (e.g. 1 modified aa per framework sequence)

2. The antibody according to statement 1 having up to 5 modified amino acids outside the CDR regions in the framework sequences.

3. The antigen binding molecule according to statement 1 or 2 wherein the antigen binding fragment is selected from the group consisting of a Fab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody.

4. The antigen binding molecule according to statement 1 or 2, which is fragment of the group consisting of a scFV, Fab, Fab2, F(ab')2, Fv or dAb.

5. The antibody according to any one of statements 1 to 4, wherein the VH CDR1 has the sequence GFIFSNYAMS [SEQ ID NO:16].

6. The antibody according to any one of statements 1 to 5, wherein the VH framework 2 has the sequence WVRQAPGKGLEWVS [SEQ ID NO:19] or WVRQAPGKGLEWGA [SEQ ID NO:20].

7. The antibody according to any one of statements 1 to 6, wherein the VH framework 3 has the sequence YSDSVKGRFTISRDNAKNTLYLQMSSLRSEDTAMYY-CAR [SEQ ID NO:23] or YADSVKGRFTISRDNAKNS-LYLQMNSLRAEDTAVYYCAR [SEQ ID NO:24].

8. The antibody according to any one of statements 1 to 7, wherein the VL framework 1 has the sequence EIVLTQSPATLSLSPGERATLSC [SEQ ID NO:30], EIVLTQSPATLSLSPGERVTMSC [SEQ ID NO:31], or EIVLTQSPATMSTSPGERVTMSC [SEQ ID NO:32].

9. The antibody according to any one of statements 1 to 8, wherein the VL CDR1 has the sequence NVSSSVSYMR [SEQ ID NO:34] or RVSSSVSYMR [SEQ ID NO:35].

10. The antibody according to any one of statements 1 to 9, wherein the VL framework 2 has the sequence WYQQKPGQAPRLLIY [SEQ ID NO:38] or WFQQKPGQAPRLWIY [SEQ ID NO:39].

11. The antibody according to any one of statements 1 to 10, wherein the VL framework 3 has the sequence GIPARFSGSGSGTDFTLTISSLEPEDFAVYYC [SEQ ID NO:43], GIPARFSGSGSGTDYTLTISSLEPEDFAVYYC [SEQ ID NO:44], GVPARFSGSGSGTDYTLTISSMEPED-FAVYYC [SEQ ID NO:45], or GVPARFSGSGSGTDYTLTISSMEPEDFAVYYC [SEQ ID NO:46].

12. The antibody according to any one of statements 1 to 11, wherein the VL CDR3 has the sequence FQGNGYPLT [SEQ ID NO:48].

13. The antibody according to any one of statements 1 to 12, wherein the VL framework 4 has the sequence FGQGTKLEIK [SEQ ID NO:51].

14. The antibody according to any one of statements 1 to 3, wherein the VH chain comprises the sequence with SEQ ID NO: 3 or SEQ ID NO: 4.

15. The antibody according to any one of statements 1 to 3, wherein the VL chain comprises the sequence with SEQ ID NO: 6, SEQ ID NO: 7, SEQ ID NO:8, SEQ ID NO: 9, SEQ ID NO: 10, SEQ ID NO: 11, SEQ ID NO: 12.

16. A nucleic acid encoding an antibody or antigen binding fragment in accordance with any one of statements 1 to 15.

17. The antibody or antigen binding fragment thereof according to any one of statements 1 to 15, for use in the treatment of a haemorrhagic complication or bleeding disorder in a subject carrying an implanted circulatory assist device.

18. The antibody or antigen binding fragment according to any one of statements 1 to 15, for use in the prevention or treatment according to statement 17, whereby said circulatory assist device implanted in said subject is a left ventricular assist device (LVAD).

19. The antibody or antigen binding fragment according to any one of statements 1 to 15, for use in the prevention or treatment according to statement 17 or 18, wherein the antibody or antigen binding fragment is administered as a bolus.

20. A method of treating or preventing a haemorrhagic complication or bleeding disorder in a subject carrying an implanted circulatory assist device comprising the step of administering to said individual a humanised monoclonal antibody or antigen binding fragment thereof binding to ADAMTS13 and inhibiting VWF cleavage by ADAMTS13 as defined in any one of statements 1 to 15.

22. Use of an antibody as defined in of any one of statements 1 to 15 in a non-human animal model with an implanted LVAD device.

23. The use according to statement 21, wherein the non-human animal is a sheep.

DETAILED DESCRIPTION OF THE INVENTION

Legends to Figures

FIG. 14 shows amino acid sequences of humanised versions of 17C7 and fragments thereof.

DETAILED DESCRIPTION

Figure 1:
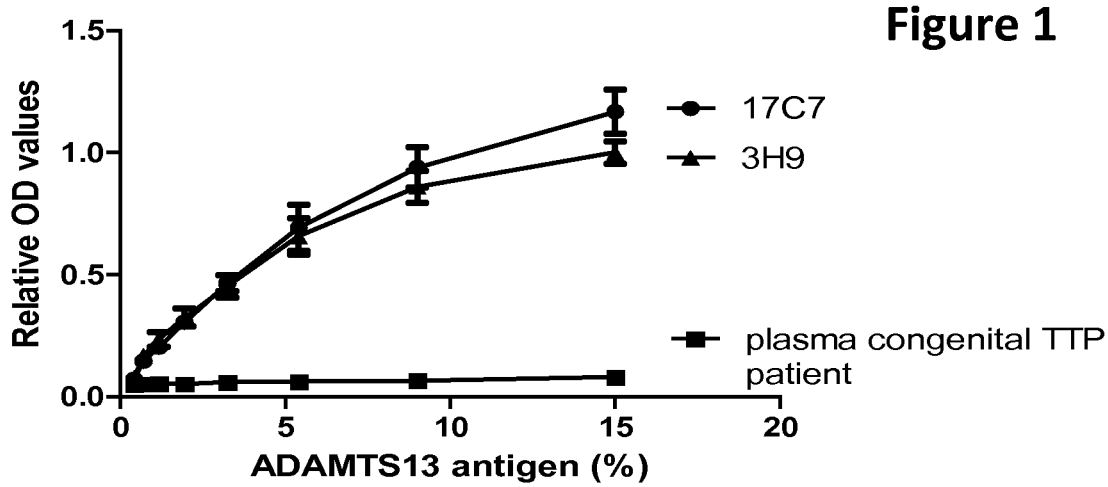
FIG. 1 shows the that 17C7 and 3H9 (Ab11316CB) antibodies specifically detect ADAMTS13 in human plasma [comparative examples].

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination. In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only. Each and every claim is incorporated into the specification as an embodiment of the present invention. Thus, the claims are part of the description and are a further description and are in addition to the preferred embodiments of the present invention.

The following terms are provided solely to aid in the understanding of the invention. Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

As used in the specification and the attached claims, the use of "a," "an" and "the" include references to plural subject matter referred to unless the context clearly dictates otherwise. Thus, for example, reference to "a protein" includes a single catalyst as well as a combination or mixture of two or more proteins, reference to "an antigen" encompasses a combination or mixture of different antigens as well as a single antigen, and the like.

A term which is subsumed under another term may be embraced by the broader term or by the more narrow specific term as appropriate within the context of the use of that term. All terms used to describe the present invention are used within context.

Except when noted, the terms "patient" or "subject" are used interchangeably and refer to a human patients.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics. Dosages can also be administered via continuous infusion (such as through a pump). The administered dose may also depend on the route of administration. For example, subcutaneous administration may require a higher dosage than intravenous administration.

In specific embodiments the dosage regime is a single administration of the antibody upon bleeding symptoms in patients with an implanted circulatory assist device.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of antibody calculated to produce a therapeutic effect in association with the carrier. The dosage unit depends on the characteristics of the antibodies and the particular therapeutic effect to be achieved. Toxicity and therapeutic efficacy of the composition can be determined by standard pharmaceutical procedures in cell cultures or experimental animals, e.g., determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Antibodies that exhibit large therapeutic indices may be less toxic and/or more therapeutically effective.

The data obtained from the cell culture assays and animal studies can be used to formulate a dosage range in humans. The dosage of these compounds may lie within the range of circulating antibody concentrations in the blood, that includes an ED50 with little or no toxicity. The dosage may vary within this range depending upon the dosage composition form employed and the route of administration. For any antibody used in the present invention, the therapeutically effective dose can be estimated initially using cell culture assays. A dose may be formulated in animal models to achieve a circulating plasma concentration range that includes the IC50 (i.e., the concentration of antibody which achieves a half-maximal inhibition of symptoms).

The terms "treating" or "treatment" include the administration of the compounds or agents of the present invention to prevent or delay the onset of the symptoms, complications, or biochemical indicia of a disease, alleviating the symptoms or arresting or inhibiting further development of the disease, condition, or disorder (e.g., LVAD induced bleeding disorder). Treatment may be prophylactic (to prevent or delay the onset of the disease, or to prevent the manifestation of clinical or subclinical symptoms thereof) or therapeutic suppression or alleviation of symptoms after the manifestation of the disease.

As used herein, "circulatory assist device" means mechanical circulatory assist (support) devices designed to be used for a wide range of clinical conditions ranging from prophylactic insertion for high-risk invasive coronary artery procedures to the management of cardiogenic shock, acute decompensated heart failure, or cardiopulmonary arrest. There are four major (arbitrary) categories of circulatory assist devices: intra-aortic balloon pump (IABP), non-IABP percutaneous mechanical circulatory assist devices, extracorporeal membrane oxygenator pumps, and nonpercutaneous centrifugal pumps, which are used for cardiopulmonary bypass.

Non-IABP percutaneous mechanical circulatory assist devices comprise continuous flow pumps. In the literature, these devices have differing names: percutaneous ventricular assist devices, percutaneous ventricular support devices, percutaneous mechanical circulatory assist devices, percutaneous mechanical circulatory support devices, and percutaneous ventricular assist devices (VADs). A ventricular assist device (VAD) is a mechanical pump that's used to support heart function and blood flow in people who have weakened hearts. This mechanical pump that is implanted inside a person's chest to help a weakened heart pump blood throughout the body. The device takes blood from a lower chamber of the heart and helps pump it to the body and vital organs, just as a healthy heart would. VADs are designed to assist either the right (RVAD) or left (LVAD) ventricle, or both at once (BiVAD). The type that is used depends primarily on the underlying heart disease and the pulmonary arterial resistance that determines the load on the right ventricle. LVADs are most commonly used, but when pulmonary arterial resistance is high, right ventricular assistance may become necessary. Unlike a total artificial heart, the LVAD doesn't replace the heart; it supports the heart. This can mean the difference between life and death for a person whose heart needs a rest after open-heart surgery, or for some patients waiting for a heart transplant (called "bridge to transplant"). LVADs may also be used as "destination therapy," which is an alternative to transplant. Destination therapy is used for long-term support in some terminally ill patients whose condition makes them ineligible for heart transplantation. An example of an LVAD is the HeartMate II® Left Ventricular Assist System (Thoratec Corporation, USA). Another example is the Impella micro-axial flow device, which is an axial flow pump which works on the principle of an Archimedes screw. The inflow is placed retrograde across the aortic valve into the left ventricle. A pump revolving at high speeds draws blood out of the left ventricle and ejects it into the ascending aorta beyond the end of the pump. Another example of a left ventricle assist device is described and displayed in U.S. Pat. No. 7,846,083.

Such mechanical circulatory support may be considered in particular clinical situations such as 1) Very high-risk percutaneous coronary intervention, including those with complex coronary artery disease involving a large territory and severe left ventricular dysfunction (ejection fraction <35 percent) or recent decompensated heart failure, 2) Complications of acute myocardial infarction, including cardiogenic shock with or without mechanical defects such as ischemic mitral regurgitation or ventricular septal rupture, 3) Advanced heart failure (during the period of stabilization of a critically ill patient while making decisions about longer-term support ("bridge-to-a-bridge")), 4) Support during high-risk percutaneous valve procedures, 5) Support for patients referred for electrophysiologic procedures with severe underlying left ventricular dysfunction who may not tolerate sustained ventricular arrhythmias during the procedure, 6) Patients with medically refractory (particularly ventricular) arrhythmias associated with ischemic and acute cardiac allograft failure or post-transplant right ventricular failure.

There is a risk of internal bleeding due to the circulatory assist device immediately after implant and during support, and episodes of post-implantation bleeding. Bleeding is the most common complication associated with the placement of a circulatory assist device and in particular of a ventricular assist device such as a LVAD. In the early experience with pulsatile LVADs, as many as 50% of patients required reoperation for bleeding. These bleeding disorders are due to the circulatory assist device placement but the mechanism is not fully understood and several causes are provided. It could be related to the effects of blood interaction with the VAD surface, to high shear stress which has previously been noted to alter the 3-dimensional structure of VWF and to enhance proteolysis of VWF by ADAMTS13, to increased platelet damage and activation, and/or to elevated platelet, leukocyte, and endothelial cell-derived microparticles in patients after VAD, indicating enhanced vascular inflammation and procoagulation.

Despite >2 decades of experience with LVADs, the incidence of major bleeding is currently still >20%. More important, newer CF pumps require anticoagulation, thereby significantly increasing bleeding-related complications at the time of cardiac transplantation and LVAD explantation, and imposing a bleeding risk throughout the duration of LVAD support.

The ADAMTS13 inhibition therapy of the present invention is to prevent or treat such bleeding disorder by humanised monoclonal ADAMTS13 antibodies, and antibody antigen binding fragments thereof.

Further, the methods and compounds of the present invention can be used to treat or prevent haemorrhagic complications or bleeding disorders caused by high shear stress in patients without implanted LVAD like patients suffering from Heyde's syndrome and patients with a veno-venous Extra Corporeal Membrane Oxygenation support (ECMO) for respiratory support.

As used herein, "ADAMTS13" shall mean "A Disintegrin And Metalloproteinase With A Thrombospondin Type 1 Motif, Member 13", also known as von Willebrand factor-cleaving protease (VWFCP). The amino acids sequence of human ADAMTS13 isoform 1 is deposited as uniprot entry Q76LX8, of human ADAMTS13 isoform 2 deposited as uniprot entry Q76LX8-2, of human ADAMTS13 isoform 3 deposited as uniprot entry Q76LX8-3 and of human ADAMTS13 isoform 4 deposited as uniprot entry Q76LX8-4.

As used herein, "VWF" shall mean "Von Willebrand factor", a blood glycoprotein involved in haemostasis.

The sequence of human VWF is deposited as uniprot entry P04275, isoform 2 is deposited as P04275-2.

It is deficient or defective in von Willebrand disease and is involved in a large number of other diseases, including thrombotic thrombocytopenic purpura, Heyde's syndrome, and inflammation. Increased plasma levels in a large number of cardiovascular, neoplastic, and connective tissue diseases are presumed to arise from adverse changes to the endothelium, and may contribute to an increased risk of thrombosis.

By "ADAMTS13 antibody" and "ADAMTS13 antibody fragment" are meant humanised monoclonal antibody and antigen binding antibody fragment, respectively, that binds to ADAMTS13. The ADAMTS13 antibodies and ADAMTS13 antibody fragments of the invention are thus antibodies and antibody fragments that specifically bind ADAMTS13. Furthermore, these antibodies and fragments inhibit proteolytic cleavage of VWF by ADAMTS13. Preferred embodiments of these antibodies allow a dose dependent inhibition whereby the concentration can be increased up to a concentration whereby a complete inhibition in an individual can be obtained.

The phrase "specifically bind(s)" or "bind(s) specifically" when referring to a peptide, refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein, for example, solid-phase ELISA immunoassays, or immunoprecipitation. Typically, a specific or selective reaction will be at least twice background signal or noise and more typically more than 10 times background. For instance, antibodies and antibody fragments of the invention preferentially bind to ADAMTS13, whereby by "preferentially binding", "preferentially recognizing" or "preferentially reacting with" is meant that the antibodies or antibody fragments show greater binding capacity for ADAMTS13 as compared to any other antigen. The binding capacity of an antibody or antibody fragment to an antigen is reflective of its affinity and/or avidity for that antigen.

Binding specificity can be expressed by association and dissociation constants as determined by ELISA or BIA-CORE.

The terms "antibody" and "antibodies" are recognized in the art and refer to proteins also known as immunoglobulins that bind to antigens. It is to be understood that these terms encompass conventional vertebrate antibodies like IgA, IgD, IgE, IgG, IgM, IgT, IgX and IgY, composed of at least two heavy and two light chains, as well as antibodies only composed of two heavy chains (VHH antibodies, IgNAR, heavy-chain antibodies, single-domain antibodies or nanobodies), and single-chain antibodies. In the case of conventional antibodies, the antigen binding sites are contributed to by the variable domains of both the heavy and light chains (VH and VL). The term "variable domain" refers to the part or domain of an antibody which is partially or fully responsible for antigen binding. Generally, variable domains will be amino acid sequences that essentially consist of 4 framework regions (FRI to FR4 respectively) and 3 complementarity determining regions (CDR1 to CDR3 respectively), or any suitable fragment of such an amino acid sequence which usually contains at least some of the amino acid residues that form at least one of the CDR's. Such variable domains and fragments are most preferably such that they comprise an immunoglobulin fold or are capable for forming, under suitable conditions, an immunoglobulin fold. Each CDR may contribute to a greater or lesser extent to antigen binding by the antibody. Single domain antibodies or heavy-chain antibodies can be found in camelids and sharks, and each of the antigen-binding sites of these antibodies is formed by a single heavy chain variable domain (VHH) only. Therefore, only three CDRs contribute to a greater or lesser extent to each antigen-binding site. Single chain antibodies (scFv) are derived from conventional antibodies by translational fusion of the VH and VL domains, separated by a flexible linker, into a single antigen-binding domain. Framework sequences of an antibody may be altered without altering the antigenic specificity of the antibody, or in order to change the binding affinity of the antibody. Furthermore, conventional antibodies may switch classes or isotypes without substantially affecting antigen-binding characteristics.

The term "complementarity determining region" or "CDR" refers to variable regions of either H (heavy) or L (light) chains (abbreviated as VH and VL, respectively) and contains the amino acid sequences capable of specifically binding to antigenic targets. These CDR regions account for the specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The accepted CDR regions and variable domains of an antibody are known to the skilled person and have been described by Padlan et al. (1995) *FASEB J.* 9, 133-139.

The skilled person is familiar with the concept that, upon alignment of corresponding CDRs of different antibodies with similar antigen specificity, the positions in the alignment which are conserved, i.e. identical in all sequences in the alignment, are critical for the antigen specificity of the antibodies. The residues of a particular CDR at these critical positions are known as "specificity-determining residues" or "SDRs". As a consequence, positions which are not conserved contribute less to the specificity of the antibodies and can be substituted without substantially affecting the antigen specificity of an antibody. Therefore, the skilled person is able to determine which residues could be substituted without substantially affecting antigen specificity of the antibody or antibody fragment. In the same way, the skilled person is able to determine the minimum sequence identity between a particular CDR of an antibody and the corresponding CDR of an antibody of the present invention, which is required for the particular CDR to have a similar antigen specificity as the corresponding CDR of an antibody of the present invention. The same holds true for the variable regions. By the term "antibody fragment" is meant a fragment of an antibody that largely retains antigen-binding capacity of the antibody from which it is derived. Therefore, an ADAMTS13 antibody fragment of the invention is capable of preferentially binding to ADAMTS13. Antigen-binding capacity is determined by the variable domain or domains, more particularly by 1, 2, 3, 4, 5 or 6 CDRs located in the VH and/or VL domains in the case of conventional and single-chain antibodies, and 1, 2 or 3 CDRs in the case of single-domain antibodies. Preferred antibody fragments of the invention therefore comprise antigen-binding sites comprising 1, 2, 3, 4, 5 or 6 CDRs. Two or more CDRs may be physically separated from each other by connecting regions to provide a framework structure for the CDRs. More preferred antibody fragments of the invention comprise antigen-binding sites comprising 1 or 2 variable domains. Examples of antibody fragments are well-known to the skilled person and include the monovalent antigen-binding fragments (Fab), bivalent F(ab')2 fragments, Fv fragments (e.g. single chain antibodies scFv), miniaturized antibodies, single-domain antibody fragments like nanobodies (Nelson A L 2010, Antibody fragments: hope and hype. mAbs 2: 77-83). Antibody fragments of the invention may be obtained by enzymatic or chemical proteolysis, or by recombinant DNA technology techniques well known to the skilled person.

Antibodies and antibody fragments of the invention may be further chemically conjugated, non-covalently bound, or translationally fused to other proteins. Single chain antibodies scFv are an example of translational fusion between a VH and a VL domain. Further examples are albumin-conjugated antibodies or antibody fragments, bivalent diabodies, and monospecific and bispecific tandem svFcs (Nelson A L 2010, Antibody fragments: hope and hype. mAbs 2: 77-83).

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, New York, pp. 269-315 (1994)). Methods for preparing single-chain antibodies are known in the art (see, for example, U.S. Pat. Nos. 4,946,778, 5,260,203, 5,091,513, and 5,455,030). In such scFvs, the heavy chain V region and the light chain V region are linked together via a linker, preferably, a polypeptide linker (Huston, J. S. et al. (1988) *Proc. Natl. Acad. Sci. USA,* 85, 5879-5883). The heavy chain V region and the light chain V region in a scFv may be derived from the same antibody, or from different antibodies.

An "Fv" fragment is the smallest antibody fragment, and contains a complete antigen recognition site and a binding site. This region is a dimer (VH-VL dimer) wherein the variable regions of each of the heavy chain and light chain are strongly connected by a noncovalent bond. The three CDRs of each of the variable regions interact with each other to form an antigen binding site on the surface of the VH-VL dimer. In other words, a total of six CDRs from the heavy and light chains function together as an antibody's antigen-binding site. However, a variable region (or a half Fv, which contains only three antigen-specific CDRs) alone is also known to be able to recognize and bind to an antigen, although its affinity is lower than the affinity of the entire binding site. Thus, a preferred antibody fragment of the present invention is an Fv fragment, but is not limited thereto.

Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody.

A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody", even when it is not identical to an antibody fragment produced by protease digestion. Fab'-SH is Fab' with one or more cysteine residues having free thiol groups in its constant region. A F(ab') fragment is produced by cleaving the disulphide bond between the cysteine residues in the hinge region of F(ab')2. Other chemically cross-linked antibody fragments are also known to those skilled in the art.

Pepsin digestion of an antibody yields two fragments; one is a F(ab')2 fragment which comprises two antigen-binding domains and can cross-react with antigens, and the other is the remaining fragment (referred to as pFc'). Herein, an antibody fragment equivalent to that obtained by pepsin digestion is referred to as a "F(ab')2-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab') 2-SH fragments can be recovered directly from hosts, such as *E. coli*, and then allowed to form F(ab')2 fragments by chemical crosslinking (Carter et al. (1992) Bio/Technology 10, 163-167).

Antibodies and antibody fragments of the invention may be further modified. Examples of such modifications include the addition of detectable enzymatic, fluorescent, luminescent, or radioactive marker groups or molecules that act in detection such as streptavidin. Other examples include the chemical modification to alter the half-life of antibodies and antibody fragments, such as PEGylation. Still other examples add effector moieties to antibodies and antibody fragments, such as toxins, radioisotopes, enzymes, cytokines, and antigens (Nelson A L (2010) *mAbs* 2, 77-83). Antibodies or antibody fragments may be further modified into an antibody-derived scaffold or antibody-like scaffolds that largely retains antigen-binding capacity of the antibody or antibody fragments from which it is derived. Examples of antibody-derived scaffolds or antibody-like scaffolds are domain antibodies (dAb) that selectively or preferentially bind the same epitope as a natural antibody, for instance dAb with fully human frameworks, for instance dAb fused to a human Fc domain or for instance nanobodies engineered in a molecule that has an IgG-like circulating half-life in humans or antibody fragments with retained antigen-binding capacity or domain antibody with active scaffolds for controlled and cell delivery.

Single domain antibodies can be engineered into antibody like fragments. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a naturally occurring single domain antibody known as heavy chain antibody devoid of light chains. Such single domain antibodies are disclosed in WO9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco or *Elasmobranchii* species for instance skates, rays (batoidea), and sharks (selachii). Other species besides *Camelidae* may produce heavy chain antibodies naturally devoid of light chain; such VHHs are within the scope of the invention. The single-chain polypeptide may be produced by various methods well known in the art such as genetic engineering technique and chemical synthesis. The genetic engineering technique includes constructing a replicable cloning vector or expression vector, transforming the host cell with the vector, culturing the transformed host cell to express the nucleic acid in it, collecting and purifying the single-chain polypeptide. The vector usually comprises the nucleic acid encoding one of the two single-chain polypeptides constituting the diabody-type bispecific antibody according to the present invention. In such case, the resulting two kinds of the vectors are preferably introduced into the same host cell.

Alternatively, the two kinds of nucleic acid encoding the different single-chain polypeptides from each other may be comprised in the same vector. The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which cannot be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell. Any cell known in the art may be used as the host cell, for example, there may be mentioned procaryotic cells such as including *E. coli*, eucaryotic cells such as mammalian cells such Chinese hamster ovary (CHO) cell and human cells, yeast, and insect cells.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilisation treatment may be carried out with the use of any agent known in the art, including alcohol such ethanol, a dissolving agent such as guanidine hydrochloride and urea.

The antibody-like fragments according to the present invention are produced by assembling the single-chain polypeptides, eventually on a scaffold, and separating and collecting the thus formed antibody-like fragments.

Assembling treatment brings the single-chain polypeptides back in an appropriate spatial arrangement in which a desired biological activity is shown. Thus, since this treatment brings the polypeptides or domains back into an assembling state, it may be considered "re-assembling." It may be also called "re-constitution" or "refolding" in view of gaining the desired biological activity.

The assembling treatment may be carried out by any method known in the art preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the formed antibody-like fragment may be done by any method known in the art as well.

VHHs, according to the present invention, and as known to the skilled addressee, are heavy chain variable domains derived from immunoglobulins naturally devoid of light chains such as those derived from Camelidae as described in WO9404678 (and referred to hereinafter as VHH domains or nanobodies). VHH molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognised by antibodies generated in vitro through the use of antibody libraries or via immunisation of mammals other than Camelids or *Elasmobranchii* species (WO 9749805). As such, anti-albumin VHH's may interact in a more efficient way with serum albumin which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO9749805), the affinity of such VHH's to circulating albumin may be increased.

The antibodies and antibody fragments of the invention are humanized. Antibody fragments derived from an antibody of the invention can be fused to the Fc region of a human antibody, in order to obtain humanized antibodies and antibody fragments. Humanized antibodies or antibody fragments can also be obtained by grafting of one or more CDRs or only their specificity-determining residues (SDRs), optionally together with one or more framework residues important for optimal CDR functionality, of a non-human antibody having the desired antigen-binding specificity, into framework polypeptide sequences of a human antibody or antibody fragment, or even into a universal humanized nanobody scaffold. Methods to humanize antibodies are well known to those skilled in the art (see e.g. (De Pascalis et al. (2002) *J Immunol.* 169, 3076-3084; Kashmiri et al. (2005) *Methods,* 36, 25-34; Almagro and Fransson (2008) Front. Biosci. 13, 1619-1633; Vincke, et al. (2009) *J Biol Chem.* 284, 3273-3284; Borras et al. J (2010) *Biol Chem.* 285, 9054-9066; Harding et al. (2010) *Mabs* 2, 256-265).

The term "humanized antibody" as used herein means a human immunoglobulin (a recipient antibody) in which at least part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in the recipient antibody or the introduced CDR or framework. These changes are made in order to optimize or improve the properties of the resulting antibody. More detailed information on these changes are referred to Jones et al. (1986) Nature, 321, 522-525; Reichmann et al. (1988) Nature 332, 323-329; EP0239400; Presta, (1992) Curr. Op. Struct. Biol. 2, 593-596; and EP0451216.

The antibody fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phages used in these methods are typically filamentous phage including fd and M13 binding domains expressed from phage with antigen-binding antibody domains recombinantly fused to either the phage gene III or gene VIII protein. Examples of phage display methods that can be used to make the antibodies or antibody fragments of the present invention include those disclosed in (Kettleborough et al. (1994) Eur. J. Immunol., 24, 952-958; Burton et al. (1994) Advances in Immunology 57, 191-280; Brinkman et al. (1995) J. Immunol. Methods, 182, 41-50; Ames et al., (1995) J. Immunol. Methods 184, 177-186; Persic et al. (1997) Gene, 187, 9-18; WO92001047; WO9110737; WO9201047; WO9218619; WO9311236; WO9515982; WO9520401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108).

After phage selection, the regions of the phage encoding the fragments can be isolated and used to generate the epitope-binding fragments through expression in a chosen host, including mammalian cells, insect cells, plant cells, yeast, and bacteria, using recombinant DNA technology. For example, techniques to recombinantly produce antigen-binding fragments can also be employed using methods known in the art such as those disclosed in WO 92/22324; Better et al., (1988) Science 240, 1041-1104; Mullinax et al. (1992) Biotechniques, 12, 864-869; Sawai et al. (1995) AJRI 34, 2634. Examples of techniques which can be used to produce single-chain Fvs and antibodies include those described in U.S. Pat. Nos. 4,946,778 and 5,258,498; Skerra et al. (1988) Science 240, 1038-1040; Huston et al. (1991) Methods in Enzymology 203, 46-88; Shu et al. (1993) PNAS 90, 7995-7999.

Changes may be made to the residues that comprise the CDRs without interfering with the ability of the antibody to recognize and bind its cognate epitope. For example, changes that do not affect epitope recognition, yet increase the binding affinity of the antibody for the epitope may be made. Several studies have surveyed the effects of introducing one or more amino acid changes at various positions in the sequence of an antibody, based on the knowledge of the primary antibody sequence, on its properties such as binding and level of expression (Yang et al. (1995) J Mol Biol. 254, 392-403; Vaughan et al. (1998) Nat Biotechnol. 16, 535-539; Rader et al. (1998) Proc Natl Acad Sci U.S.A. 95, 8910-8915). In these studies (so called affinity maturation techniques), altered versions of the antibody have been generated by changing the sequences of the encoding genes in the CDR1, CDR2, CDR3, or framework regions, using methods such as oligonucleotide-mediated site-directed mutagenesis, cassette mutagenesis, error-prone PCR, DNA shuffling, or mutator-strains of E. coli (Vaughan et al. (1998) Nat Biotechnol. 16, 535-539). These methods of changing the sequence of the antibody have resulted in improved affinities of the resulting antibodies (Gram et al. (1992) Proc Natl Acad Sci U.S.A. 89, 3576-3580; Davies and Riechmann (1996) Immunotechnology, 2, 169-179; Thompson et al. (1996) J Mol Biol. 256, 77-88; Boder et al. (2000) Proc Natl Acad Sci U.S.A. 97, 10701-10705; Furukawa et al. (2001) J Biol Chem. 276, 27622-27628; Short et al. (2002) J Biol Chem. 277, 16365-16370).

The antibodies of the invention are humanised monoclonal antibodies. The term "monoclonal antibody" is well recognized in the art and refers to an antibody or a homogenous population of antibodies that is derived from a single clone. Individual antibodies from a monoclonal antibody population are essentially identical, in that minor naturally occurring mutations may be present. Antibodies from a monoclonal antibody population show a homogenous binding specificity and affinity for a particular epitope.

As used herein, "percentage identity" or "% identity" between two or more amino acid sequences or two or more nucleotide sequences refers to the ratio, expressed in %, of: the number of amino acids or nucleotides in an optimal alignment of the amino acid sequences or nucleotide sequences that are identical in both sequences (i.e. match), to the length of the alignment, i.e. the number of aligned positions, including gaps if any.

As used herein, "cell line" is to be understood a homogenous population of eukaryotic cells which is genetically stable and can be cultured. Preferably, the cell line is of animal origin. More preferably, the cell line is immortalized. Alternatively, the cell line is of plant or fungal origin. In one embodiment, the cell line of the invention is obtained by genetic transformation with a nucleic acid comprising a polynucleotide encoding the antibody or antibody fragment of the invention under suitable transcriptional and translational control elements, which are known to those skilled in the art, to allow efficient production of the antibody or antibody fragment.

The term "nucleic acid" is intended to include DNA molecules and RNA molecules. A nucleic acid can be single-stranded or double-stranded.

The nucleic acids of the invention are present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCI banding, column chromatography, agarose gel electrophoresis and others well known in the art. see, e.g., Sambrook, Tijssen and Ausubel. The nucleic acid sequences of the invention and other nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipition reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from such sequences described herein are contemplated (where "derived" indicates that a sequence is identical or modified from another sequence).

The present invention disclosed humanized antibodies or fragments thereof of for instance a single-chain antibody, Fv fragment, a Fab fragment (e.g. Fab' fragment or a F(ab')2 fragment) or a single domain antibodies, or a human antibody or fragment thereof.

In a preferred embodiment, said isolated ADAMTS13 antibody, antibody-like scaffold or antibody fragment of the present invention is for use in the treatment of a haemorrhagic complication or bleeding disorder in a subject carrying an implanted circulatory assist device. Typically, said haemorrhagic complication or bleeding disorder is due to said implanted circulatory assist device. Preferably said subject is a mammal, more preferably said subject is a human. Preferably, said circulatory assist device is a ventricular assist device. More preferably, said circulatory assist device is a left ventricular assist device (LVAD).

The present invention presents an isolated cell line producing the antibody or antibody fragments of the present invention. In one embodiment, the cell line of the invention is obtained by genetic transformation with a nucleic acid comprising a polynucleotide encoding the antibody or antibody fragment of the invention under suitable transcriptional and translational control elements, which are known to those skilled in the art, to allow efficient production of the antibody or antibody fragment.

The present invention also provides a pharmaceutical composition comprising said ADAMTS13 antibody, antibody-like fragment or antibody fragment, for use in the prevention or treatment of a haemorrhagic complication or bleeding disorder in a subject carrying an implanted circulatory assist device. Typically, said haemorrhagic complication or bleeding disorder is due to said implanted circulatory assist device. Preferably, said subject is a mammal, more preferably, said subject is a human. Preferably, said circulatory assist device is a ventricular assist device. More preferably, said circulatory assist device is a left ventricular assist device.

The present invention also provides a method of treatment or prevention of a haemorrhagic complication or bleeding disorder in a subject carrying an implanted circulatory assist device, comprising administering to said subject said ADAMTS13 antibody, antibody-like scaffold or antibody fragment. Typically, said haemorrhagic complication or bleeding disorder is due to said implanted circulatory assist device. Preferably, said subject is a mammal, more preferably said subject is a human. Preferably, said circulatory assist device is a ventricular assist device. More preferably, said circulatory assist device is a left ventricular assist device.

The present invention presents a molecule that is an antibody, antibody-like scaffold or antibody fragment that binds ADAMTS13 for use in the treatment or prevention of a haemorrhagic complication or bleeding disorder in a subject carrying an implanted circulatory assist device. Typically, said haemorrhagic complication or bleeding disorder is due to said implanted circulatory assist device. Preferably, said circulatory assist device is a ventricular assist device. More preferably, said circulatory assist device is a left ventricular assist device.

The present invention presents humanised monoclonal antibodies capable of binding to human ADAMTS13 for use in the treatment or prevention of a haemorrhagic complication or bleeding disorder in a subject carrying an implanted circulatory assist device. Typically, said haemorraghic complication or bleeding disorder is due to said implanted circulatory assist device. Preferably, said circulatory assist device is a ventricular assist device. More preferably, said circulatory assist device is a left ventricular assist device.

In another preferred embodiment, said ADAMTS13 binding or inhibiting molecule is selected from the group consisting of aFab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody and capable of binding to human ADAMTS13. In another preferred embodiment, ADAMTS13 binding or inhibiting molecule is an ADAMTS13 antigen-binding fragment of a humanised monoclonal antibody of the group consisting of a scFV, Fab, Fab2, F(ab')2, Fv or dAb and capable of binding to human ADAMTS13.

In a preferred embodiment, said ADAMTS13 binding molecule comprises an antibody, or antigen-binding fragment thereof, that binds to ADAMTS13 with a dissociation constant (K D) of 50 nM or less, 20 nM or less, 5 nM or less, 1 nM or less, 500 pM or less, 150 pM or less, 150 pM or less, 125 pM or less, 100 pM or less as determined by real-time biospecific interaction analysis (BIA) using surface plasmon resonance (SPR) technology, or with an IC50 of 50 nM or less, 20 nM or less, 5 nM or less, 1 nM or less, 500 pM or less, 100 pM or less, 75 pM or less, 50 pM or less.

In another preferred embodiment, said ADAMTS13 binding molecule comprises an antibody, or antigen binding fragment thereof, that binds to a neutralizing epitope of human ADAMTS13 with an affinity of at least about $5\times10^4$ liter/mole as measured by an association constant (Ka), or of at least $5\times10^5$ liter/mole, or of at least $5\times10^6$ liter/mole, or of at least $1\times10^7$ liter/mole, or of at least $1\times10^7$ liter/mole.

In another preferred embodiment, said ADAMTS13 inhibitor further comprises a component selected from the group consisting of pharmaceutically acceptable carriers, diluents and excipients.

In another preferred embodiment, said circulatory assist device implanted in said subject is a ventricular assist device (VAD). In an even more preferred embodiment, said circulatory assist device implanted in said subject is a left ventricular assist device (LVAD).

The present invention relates to humanised antibody specifically binding to ADAMTS13 and inhibiting VWF cleavage by ADAMTS13 or an antigen binding fragment thereof. These humanized antibodies are defined by a variable heavy (VH) chain and a variable light [VL] chain.

In the variable heavy (VH) chain, the following sequence elements are present:
a Framework 1 having the sequence EVQLVESGG-GLVKPGGSLRLSCAAS [SEQ ID NO: 14], a CDR1 region having the sequence GFIFS[NQSAD]
YAMS [SEQ ID NO:15].

Herein the amino acids between square brackets are alternatives for a certain amino acid at a given amino acid following the format of Prosite. Thus in the above sequence amino acid 6 [NQSAD] can be Asn, Gln, Ser, Ala or Asp.

- a Framework 2 having the sequence WVRQAPGK-GLEW[VG][SA] [SEQ ID NO:17],
- a CDR2 region having the sequence TITTGGFYTF [SEQ ID NO:21],
- a Framework 3 having the sequence Y[AS]DSVKGRFTISRDNAKNSLYLQMNSLRAEDTA[VM]YYCAR [SEQ ID NO:22],
- a CDR3 region having the sequence HRYDDYYALDY [SEQ ID NO:25], and
- a Framework having the sequence WGQGTLVTVSS [SEQ ID NO:27], In the variable light (VL) chain, the following sequence elements are present:

- a framework 1 having the sequence E[I]VLTQSPAT[LM]S[LT]SPGER[AV]T[LM]SC [SEQ ID NO:28],
- a CDR1 region having the sequence [RNQSAD]VSSSVSYMR [SEQ ID NO:33],
- a framework 2 having the sequence W[YF]QQKPGQ[AS]PRL[LW]IY [SEQ ID NO:36],
- a CDR2 region having the sequence DTSKLAS [SEQ ID NO:40],
- a framework 3 having the sequence G[IV]PARFSGSGSGTD[FY]TLTISS[LM]EPED[FV]AVYYC [SEQ ID NO:41],
- a CDR3 region having the sequence FQG[NQSA]GYPLT [SEQ ID NO:47], and
- a framework 4 having the sequence FGQGTKLE[IL]K [SEQ ID NO:49].

It is envisaged that additional minor substitutions can be made in the framework region without influencing antigen binding or immunicity. Thus embodiments of the humanized antibodies of the present invention may contain for the above defined VH or VL chain up to 10, 8, 5, 3 modified amino acids outside the CDR regions.

Using the above mentioned humanized monoclonal antibodies is possible to engineer fragment is selected from the group consisting of a Fab', F(ab')2, Fab, Fv, vIgG, scFv fragments and surrobodies, rIgG, disulfide-stabilized Fv antibodies (dsFv), diabodies, triabodies, and single domain antibodies, such as a camelized antibody or nanobody or humanized camel or shark antibody or nanobody, in particular a fragment selected from the group consisting of a scFV, Fab, Fab2, F(ab')2, Fv or dAb.

In specific embodiments VH CDR1 has the sequence GFIFSNYAMS [SEQ ID NO:16].

In specific embodiments the VH framework 2 has the sequence WVRQAPGKGLEWVS [SEQ ID NO:19] or WVRQAPGKGLEWGA [SEQ ID NO:20].

In specific embodiments the VH framework 3 has the sequence YSDSVKGRFTISRDNAKNTLYLQMSSLRSEDTAMYYCAR [SEQ ID NO:23] or YADSVKGRFTISRDNAKNSLYLQMNSLRAEDTAVYYCAR [SEQ ID NO:24].

In specific embodiments the VL framework 1 has the sequence EIVLTQSPATLSLSPGERATLSC [SEQ ID NO:30], EIVLTQSPATLSLSPGERVTMSC [SEQ ID NO:31], or EIVLTQSPATMSTSPGERVTMSC [SEQ ID NO:32].

In specific embodiments VL CDR1 has the sequence NVSSSVSYMR [SEQ ID NO:34] or RVSSSVSYMR [SEQ ID NO:35].

In specific embodiments the VL framework 2 has the sequence WYQQKPGQAPRLLIY [SEQ ID NO:38] or WFQQKPGQAPRLWIY [SEQ ID NO:39].

In specific embodiments the VL framework 3 has the sequence GIPARFSGSGSGTDFTLTISSLEPEDFAVYYC [SEQ ID NO:43], GIPARFSGSGSGTDYTLTISSLEPEDFAVYYC [SEQ ID NO:44], GVPARFSGSGSGTDYTLTISSMEPEDFAVYYC [SEQ ID NO:45], or GVPARFSGSGSGTDYTLTISSMEPEDFAVYYC [SEQ ID NO:46].

In specific embodiments the VL CDR3 has the sequence FQGNGYPLT [SEQ ID NO:48]. In specific embodiments the VL framework 4 has the sequence FGQGTKLEIK [SEQ ID NO:51].

In specific embodiments the VH chain comprises the sequence with SEQ ID NO: 3 or SEQ ID NO: 4.

In specific embodiments VL chain comprises the sequence with SEQ ID NO: 6, SEQ ID NO: 7, SEQ ID NO:8, SEQ ID NO: 9, SEQ ID NO: 10, SEQ ID NO: 11, SEQ ID NO: 12.

Any combination of the above 2 VH chains with the above 7 VL chains is envisaged.

EXAMPLES

Example 1: Characterization of 17C7 and Human Plasma

Monoclonal Anti-ADAMTS13 Antibody 17C7 Captures Human ADAMTS13 from Human Plasma A 96-well plate was coated with 17C7 or 3H9 (Ab11316CB) (5 µg/mL), blocked and a serial dilution of normal human plasma (NHP) or plasma of a congenital TTP patient was added (15% in first well, 1.5/2.5 dilution). Bound ADAMTS13 was detected with in house developed biotinylated monoclonal anti-ADAMTS13 antibodies 17G2 and 19H4 (1.5 µg/mL) followed by addition of streptavidin labelled with horse radish peroxidase (HRP). Colouring reaction was performed with orthophenylene diamine (OPD) and $H_2O_2$. The reaction was stopped with $H_2SO_4$. Data are represented as mean+/−SD, n=3.

When coating a constant concentration of 17C7 or 3H9 (Ab11316CB) and adding a dilution series of normal human plasma, both monoclonal anti-ADAMTS13 antibodies 17C7 and 3H9 (Ab11316CB) efficiently capture human ADAMTS13 from human plasma (FIG. 1).

3H9 has the following VH and VL chains:

```
3H9 variable heavy chain:
                                           [SEQ ID NO: 52]
EVQLVESGGD LVKPGGSLKL SCAASGFTFS SYGMSWVRQT

PDKRLEWVAT ISSGGTYTYY ADTVKGRFTI SRDNAKNTLY

LQMSSLTSED SAMFYCARRV AWDFGSTYDY AMDYWGQGTT

VT

VHCDR1
                                           [SEQ ID NO: 53]
GFTFSSYG

VHCDR2
                                           [SEQ ID NO: 54]
ISSGGTYT

VHCDR3
                                           [SEQ ID NO: 55]
ARRVAWDFGSTYDYAMDY

3H9 variable light chain:
                                           [SEQ ID NO: 56]
DIELTQSPAT LSVTPGDRVG LSCRASQSLS NYLHWYQQKS

HESPRLLINY ASQSISGIPS RFSGSGSGTD FTLSINSVET
```

-continued

EDFGMCFCQQ SNSWPLTFGA GTKL

VLCDR1 [SEQ ID NO: 57]

QSLSNY

VLCDR2

YAS

VLCDR3 [SEQ ID NO: 58]

QQSNSWPLT

Monoclonal Anti-ADAMTS13 Antibody 17C7 Has a Higher Affinity for ADAMTS13 Than Monoclonal Anti-ADAMTS13 Antibody 3H9 (Ab11316CB)

Figure 2:
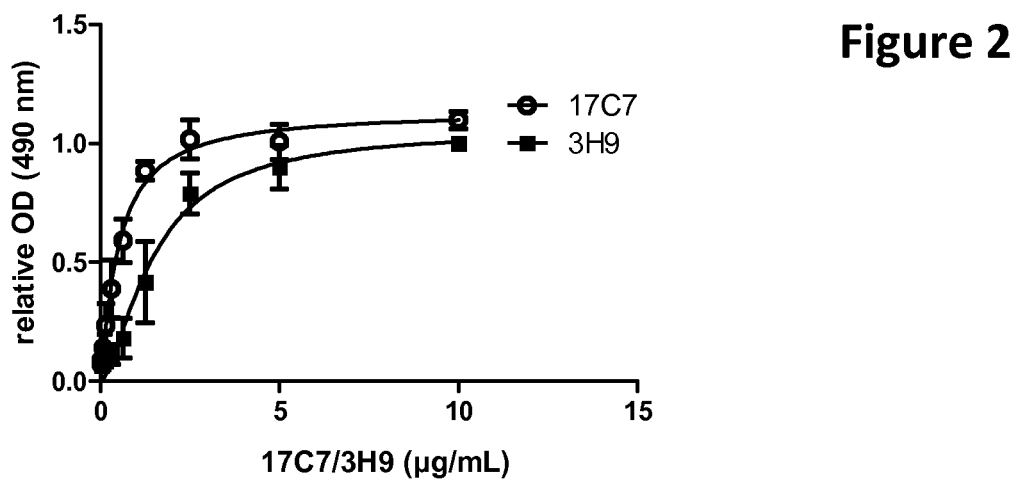
FIG. 2 shows the difference of affinity of ADAMTS13 for the 17C7 and 3H9 (Ab11316CB) antibody in capturing ADAMTS13 from plasma [comparative examples].

A 96-well plate was coated with a serial dilution of either 17C7 or 3H9 (Ab11316CB) (ranging from 10 µg/mL to 0.02 µg/mL), blocked and a constant amount of normal human plasma (15%) was added. Detection of bound ADAMTS13 occurred as descripted in 1.1. Data are represented as mean+/−SD, n=3. Lines were fitted by nonlinear regression. When coating a dilution series of 17C7 or 3H9 and adding a constant amount of normal human plasma, half maximal binding ($K_d$) of human ADAMTS13 was observed at 0.51 µg/mL for 17C7 and 1.5 µg/mL for 3H9 (Ab11316CB) showing that 17C7 has a higher affinity for ADAMTS13 in human plasma than 3H9 (Ab11316CB) (FIG. 2).

Figure 3:
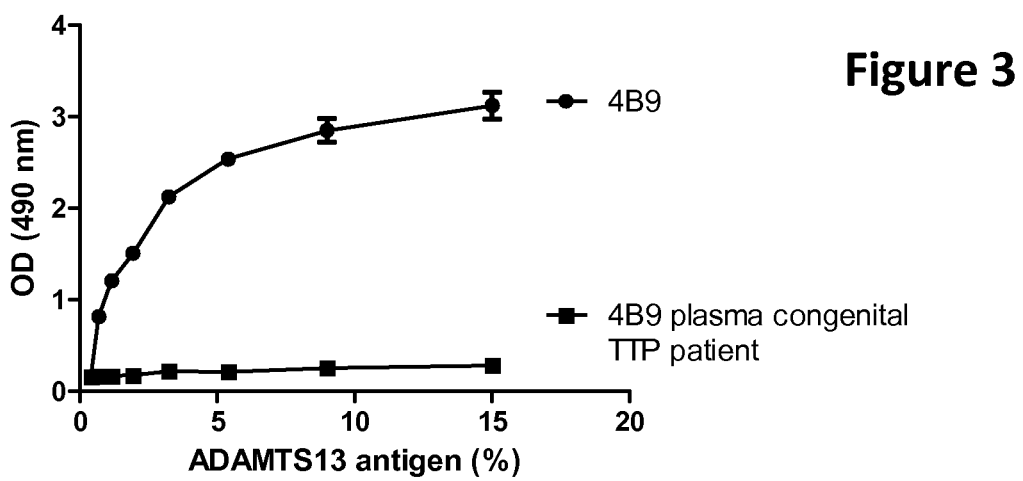
FIG. 3 shows that 17C7 can also detect ADAMTS13 in plasma, when ADAMTS13 is captured by the other anti-ADAMTS13 antibody 4B9 [comparative examples].
Figure 4:
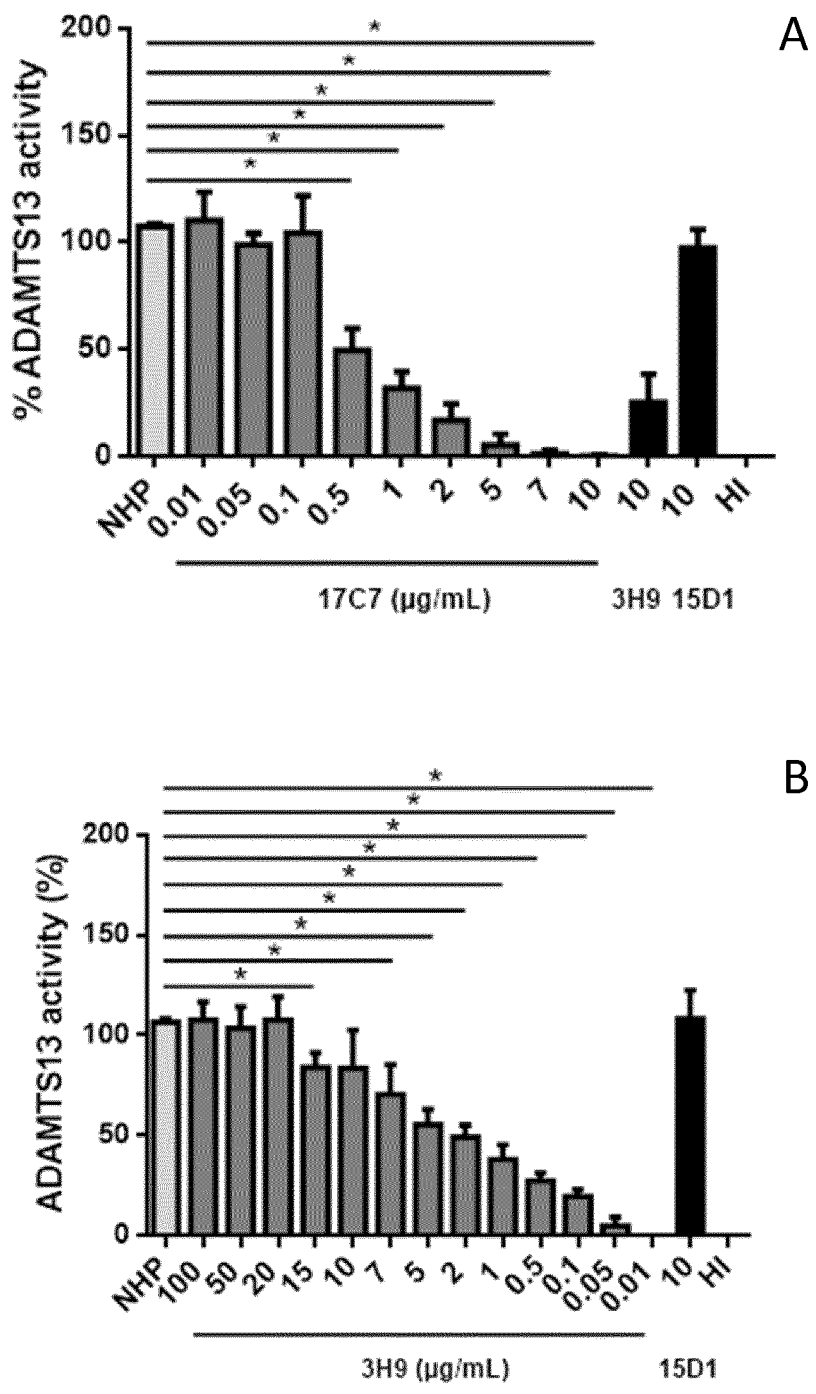
FIGS. 4 and 5 show the inhibitory effect of the 17C7 and 3H9 (Ab11316CB) antibody on ADAMTS13 activity [comparative examples].

Monoclonal Biotinylated Anti-ADAMTS13 Antibody 17C7 Detects Human ADAMTS13 from Human Plasma A 96-well plate was coated with the anti-ADAMTS13 monoclonal antibody 4B9 (5 µg/mL), blocked and a serial dilution of normal human plasma or plasma of a congenital TTP patient was added (15% in first well, 1.5/2.5 dilution), bound ADAMTS13 was detected with biotinylated anti-ADAMTS13 monoclonal antibody 17C7 (1.5 µg/mL) followed by addition of streptavidin labelled with horse radish peroxidase (HRP). Colouring reaction was performed with orthophenylene diamine (OPD) and $H_2O_2$. The reaction was stopped with $H_2SO_4$. Data are represented as mean+/−SD, n=2. When coating a constant amount of monoclonal anti-ADAMTS13 antibody 4B9, biotinylated 17C7 efficiently detects human ADAMTS13 from normal human plasma (FIG. 3).

Monoclonal Anti-ADAMTS13 Antibody 17C7 is a More Potent Inhibitor of Human ADAMTS13 Than Monoclonal Anti-ADAMTS13 Antibody 3H9 (Ab11316CB)

Figure 5:
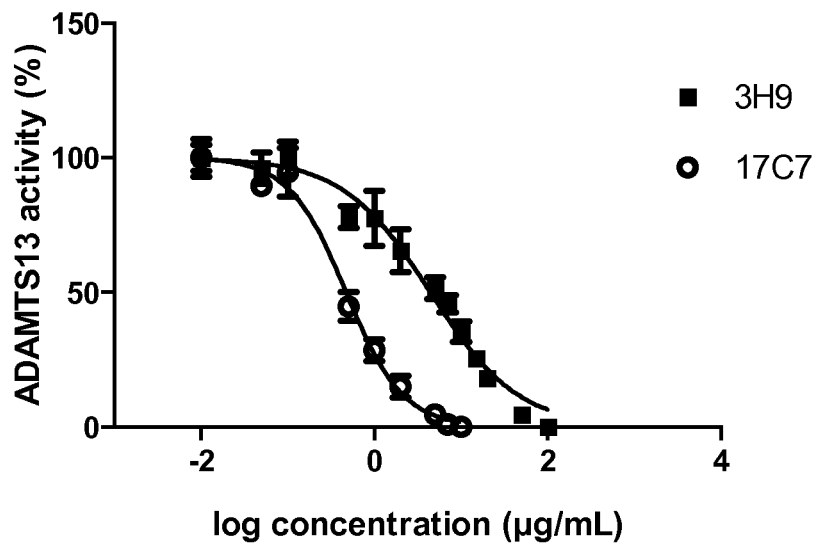
Figure 11:
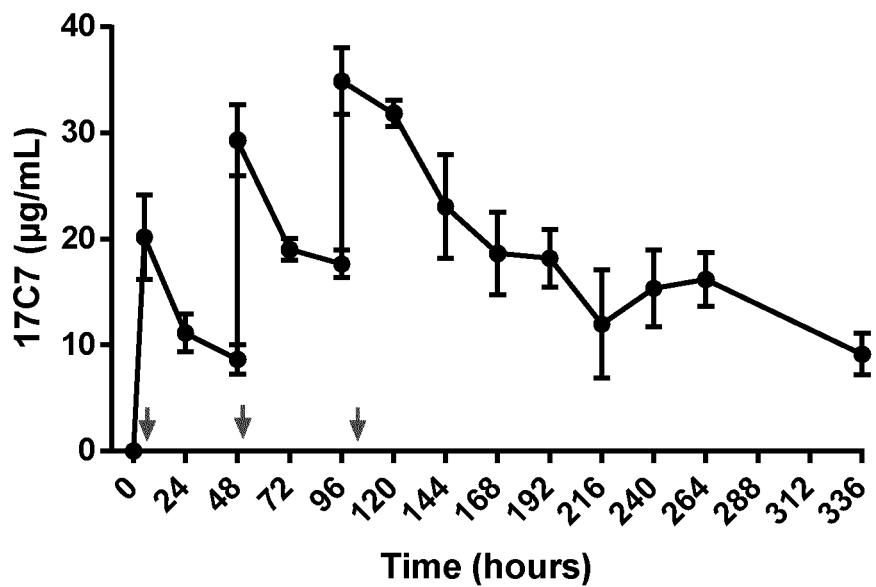
FIG. 11 shows antibody plasma levels of the 17C7 antibody in sheep.

Normal human plasma was pre-incubated for 15 minutes with different concentrations of 17C7 or 3H9 (Ab11316CB). ADAMTS13 activity in plasma was determined using the FRETS-VWF73 assay (Kokame et al. (2005) *Br J Haematol.* 129, 93-100) (FIGS. 11 A and B). ADAMTS13 activity in NHP was set at 100%. Non-inhibitory anti-ADAMTS13 monoclonal antibody 15D1 was used as a control. When incubating NHP with different concentrations of anti-ADAMTS13 antibodies 17C7 or 3H9 (Ab11316CB), half maximal inhibitory concentration (IC50) was observed at 0.47 µg/mL for 17C7 and 4.43 µg/mL for 3H9 (Ab11316CB) showing that 17C7 is a more potent inhibitor of human ADAMTS13 activity than 3H9 (FIG. 5).

Example 2: Characterization of 17C7 and Ovine Plasma

Cross Reactivity of Monoclonal Anti-ADAMTS13 Antibody 17C7 with Ovine ADAMTS13

Figure 6:
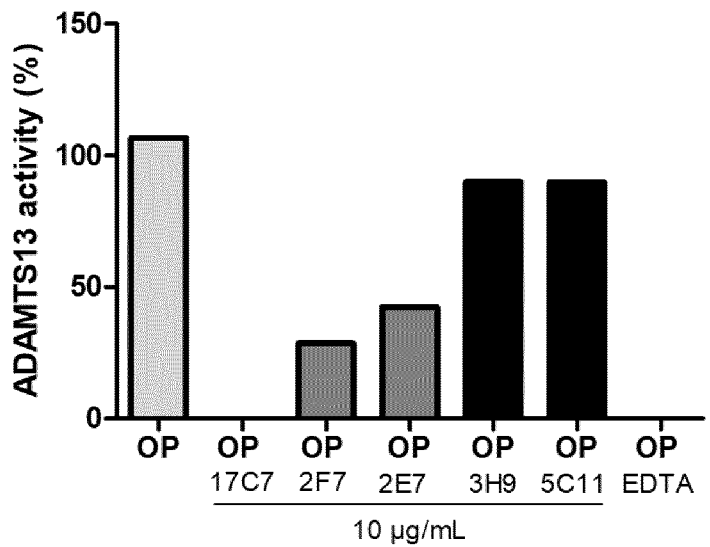
FIG. 6 shows the cross reactivity of the 17C17 antibody with sheep ADAMTS13 via inhibition of sheep ADAMTS13 activity [comparative examples].

ADAMTS13 activity in plasma was determined using the FRETS-VWF73 assay. Inhibition of ADAMTS13 in ovine plasma (OP) was studied using different anti-ADAMTS13 antibodies. The activity of ovine ADAMTS13 in ovine plasma was set at 100%. Anti-ADAMTS13 antibody 17C7 is capable of inhibiting ovine ADAMTS13, while the anti-ADAMTS13 monoclonal antibodies 3H9 (Ab11316CB) and 5C11 are not. As a control EDTA (Ethylenediaminetetraacetic acid, a chelator of $Zn^{2+}$ and $Ca^{2+}$, which are necessary for the activity of ADAMTS13) was added (FIG. 6).

Monoclonal Anti-ADAMTS13 Antibody 17C7 is a Potent Inhibitor of Ovine ADAMTS13

Ovine plasma (OP) was pre-incubated for 15 minutes with different concentrations of 17C7. ADAMTS13 activity in plasma was determined using the FRETS-VWF71 assay (Muia et al. (2013) *J. Thromb. Haemostas.* 11, 1511-1518) (FIG. 7A). ADAMTS13 activity in ovine plasma was set at 100%. When incubating ovine plasma with different concentrations of anti-ADAMTS13 antibody 17C7 half maximal inhibitory concentration (IC50) was observed at 2.4 µg/mL (FIG. 7B).

Example 3: Left Ventricular Assist Device Implantation in Sheep

Figure 8:
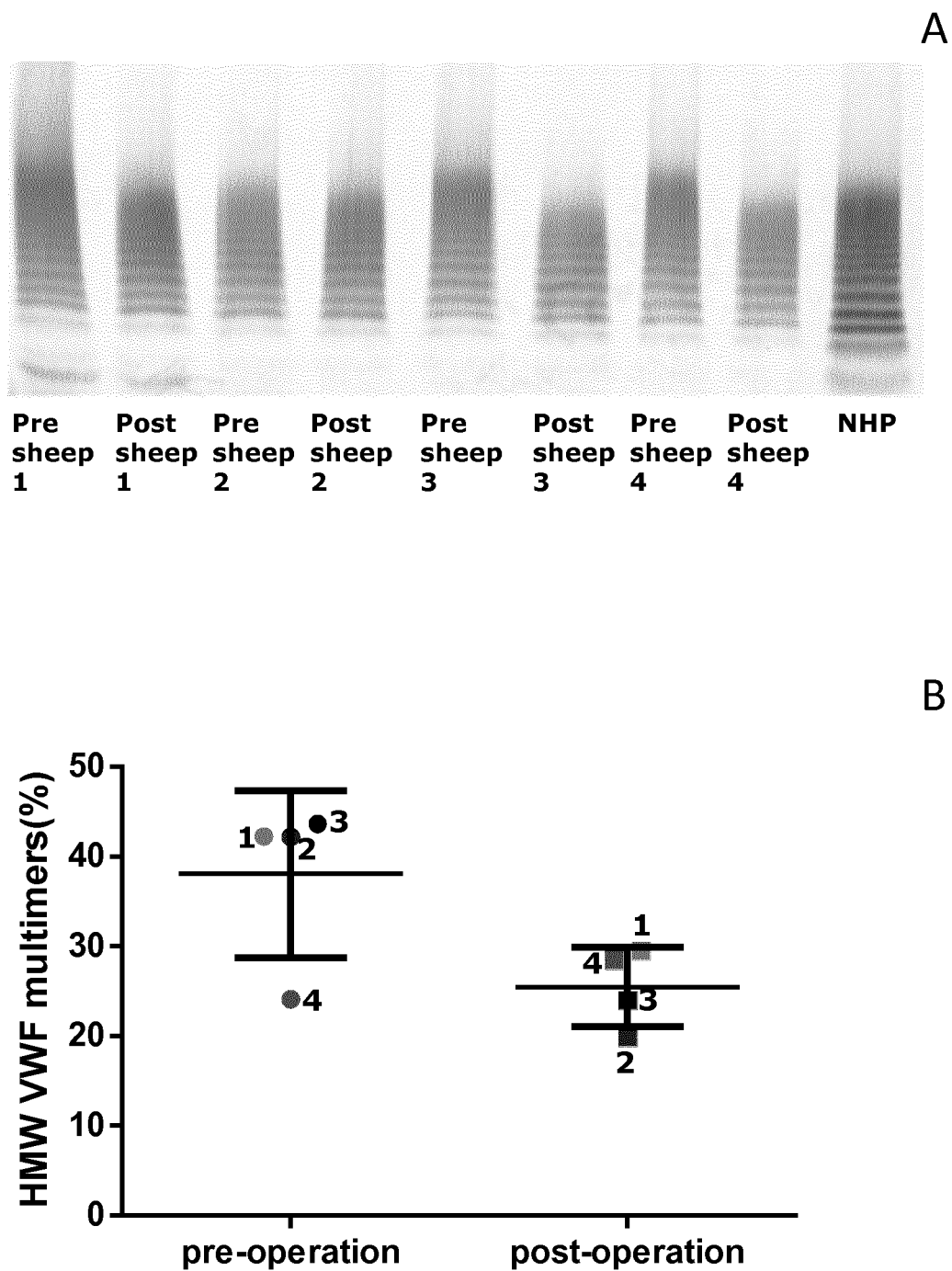
FIG. 8 shows the determination of vWF multimers before and after LVAD implantation in sheep.

VWF Multimeric Profile in Sheep Before and After Implantation of a Left Ventricular Assist Device Blood samples were taken before (Pre) and after (Post) implantation of a left ventricular assist device (Impella, Abiomed, Germany, Aachen) device in 4 sheep. The plasma samples were loaded on a 0.8% stacking and 1.2% running agarose gel. After running the gel, the gel was dried and incubated with an alkaline phosphatase labelled anti-human VWF antibody. Next, a colouring reaction was performed to visualize the VWF multimer pattern (FIG. 8A). To calculate the percentage of low molecular weight (LMW) VWF, medium molecular weight (MMW) VWF and high molecular weight (HMW) VWF multimers, densitometric analysis was performed using Image.) software (version 1.47, National Institute of Health, Bethesda, USA). For each lane, the complete multimer was selected and the density was graphed. The lowest 5 (1-5 mer), the medium (6-10 mer), and the high molecular weight (HMW; >10 mer) multimers were selected and the density of the HMW multimers relative to the complete multimer was calculated as a percentage. Mean data of the LMW, MMW and HMW VWF multimers are presented in FIG. 8B. For 3 of the 4 sheep, HMW VWF multimers decreased after Impella implantation.

Figure 9:
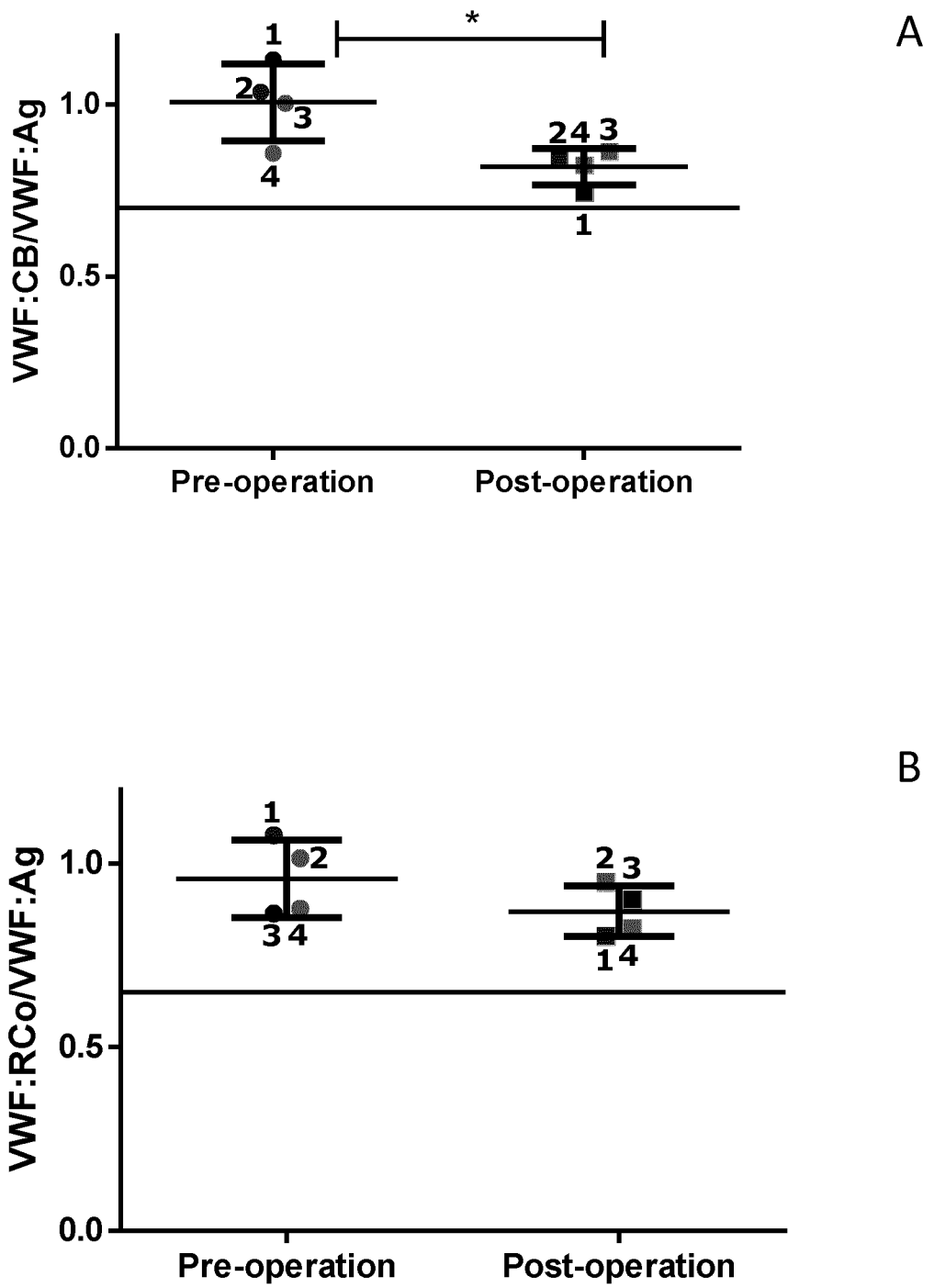
FIG. 9 shows collagen binding and ristocetin cofactor activity of VWF before and after implantation of an LVAD.

Collagen Binding and Ristocetin Cofactor Activity of Ovine VWF Before and after Implantation of a Left Ventricular Assist Device Binding of VWF to its ligands collagen and platelet glycoprotein (GP) Ib was determined via ELISA. To determine the collagen binding activity (VWF:CB), 25 µg/mL of human collagen type III was coated on a 96-well ELISA plate, ovine plasma was added and bound VWF was detected with polyclonal anti-human VWF antibodies labelled with horse radish peroxidase (HRP). Colouring reaction was performed with orthophenylene diamine (OPD) and $H_2O_2$. The reaction was stopped with $H_2SO_4$. To measure the VWF ristocetin cofactor activity (VWF:RCo) (Vanhoorelbeke et al., (2000) *Thrombosis and haemostasis* 83, 107-113), 5 μg/mL of anti-GPIb monoclonal antibody 2D4 was coated on a 96-well ELISA plate and a recombinant fragment of GPIb was captured. Next, ovine plasma containing VWF was added in the presence of ristocetin, which allows binding of VWF to GPIb under static conditions, and bound VWF was detected with anti-VWF antibodies labelled with HRP. Colouring reaction was performed with orthophenymene diamine (OPD) and $H_2O_2$. The reaction was stopped with $H_2SO_4$. Ovine plasma before implantation of the left ventricular assist device was used as a reference and the activity was set at 100%. Next the ratio of VWF:CB over VWF antigen (VWF:Ag) (VWF:CB/VWF:Ag) (FIG. 9A) or VWF:RCo over VWF:Ag (VWF:RCo/VWF:Ag) (FIG. 9B) was calculated. As expected, the mean VWF:CB/VWF:Ag ratio was significantly decreased after implantation of the left ventricular assist device but this was not the case for the VWF:RCo/VWF:Ag ratio.

Example 4: Monoclonal Anti-ADAMTS13 Antibody 17C7 Injection in a Naïve Sheep

In Vivo Inhibition of Sheep ADAMTS13

Figure 7:
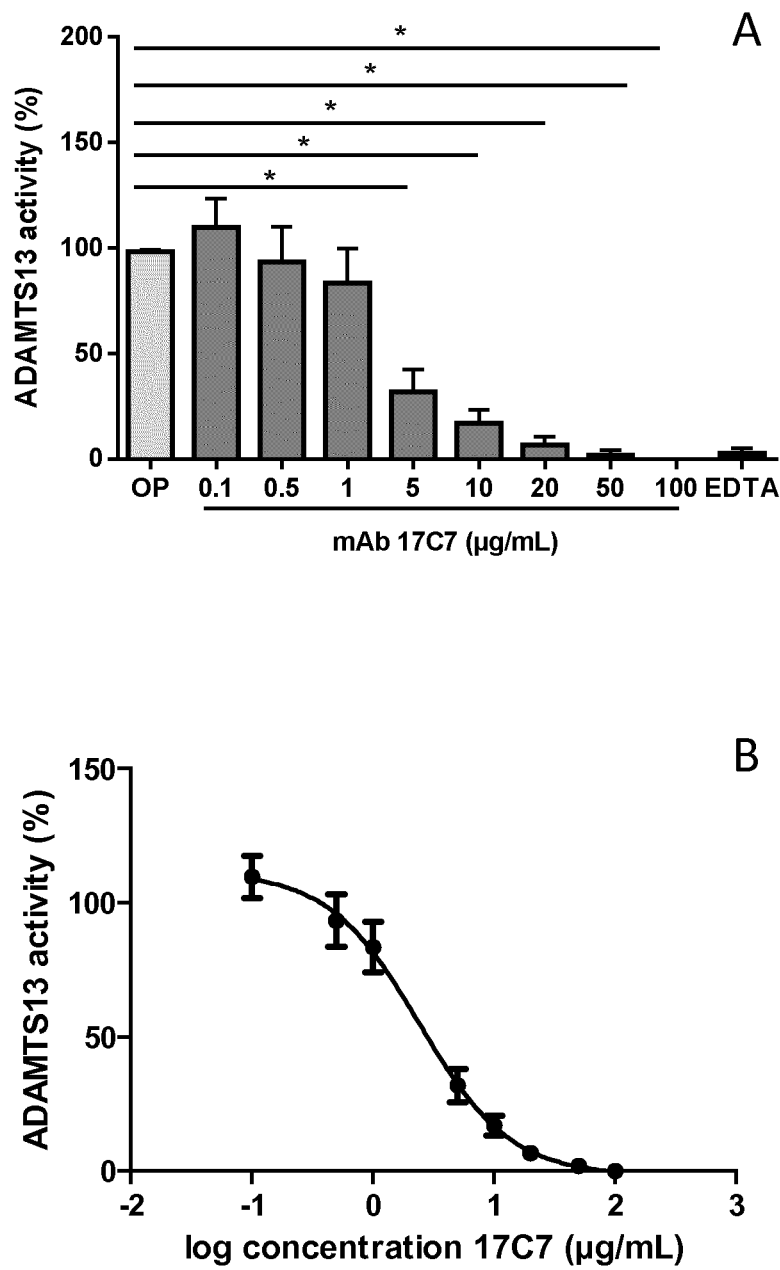
FIG. 7 shows a dose response of the inhibitory effect of the 17C17 antibody on sheep ADAMTS13 activity [comparative examples].
Figure 10:
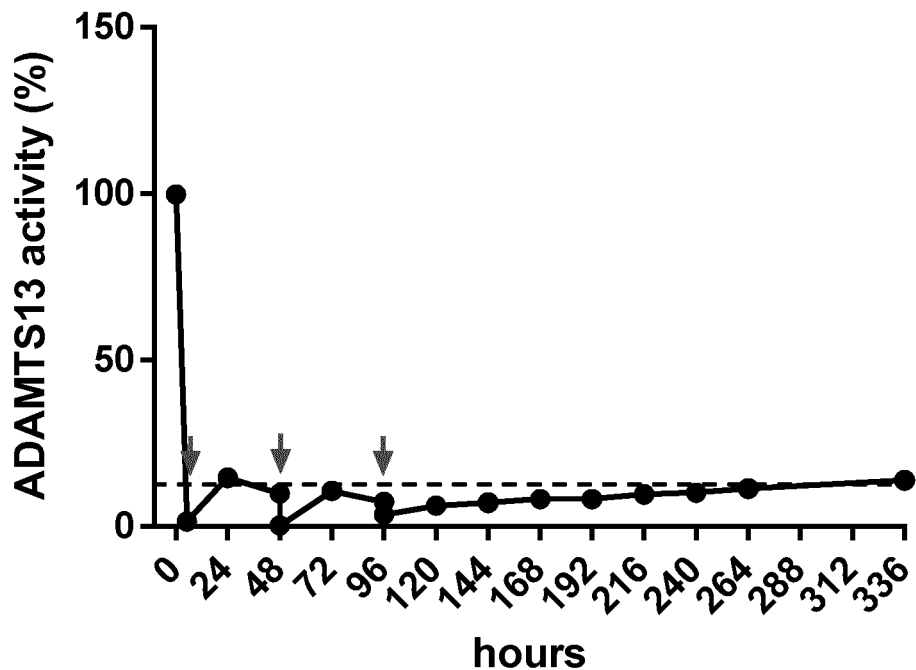
FIG. 10 shows the in vivo inhibition of sheep ADAMTS13 by the 17C7 antibody.

A dose of 600 μg/kg monoclonal anti-ADAMTS13 antibody 17C7 was injected in one sheep every 48 hours. Blood samples were collected before and 2 minutes after each injection of 17C7 (red arrows). In addition, blood samples were collected every 24 hours. ADAMTS13 activity in plasma was determined using the FRETS-VWF71 assay (FIG. 7). ADAMTS13 activity at baseline levels (0 hours) was set as 100%. Ovine ADAMTS13 activity was fully inhibited until 14 days after the first injection (FIG. 10).

Antibody Levels in Plasma in a Sheep Injected with Monoclonal Anti-ADAMTS13 Antibody 17C7

A 96-well ELISA plate was coated with 5 μg/mL goat anti-mouse (GAM) IgG Fab specific antibodies, ovine plasma was added and bound monoclonal anti-ADAMTS13 antibody 17C7 was detected with GAM antibodies labelled with horse radish peroxidase (HRP). Colouring reaction was performed with orthophenylene diamine (OPD) and $H_2O_2$. The reaction was stopped with $H_2SO_4$. A dilution series of phosphate-buffered saline (PBS) spiked with a known concentration of 17C7 was used as a calibration curve to calculate the plasma levels of 17C7. Injection of 17C7 in the sheep resulted in a mean initial plasma concentration of 20 μg/mL and then declined after 14 days to 10 μg/mL (FIG. 11).

VWF Antigen Levels and VWF Collagen Binding Activity in Plasma of a Sheep Injected with Monoclonal Anti-ADAMTS13 Antibody 17C7

Figure 12:
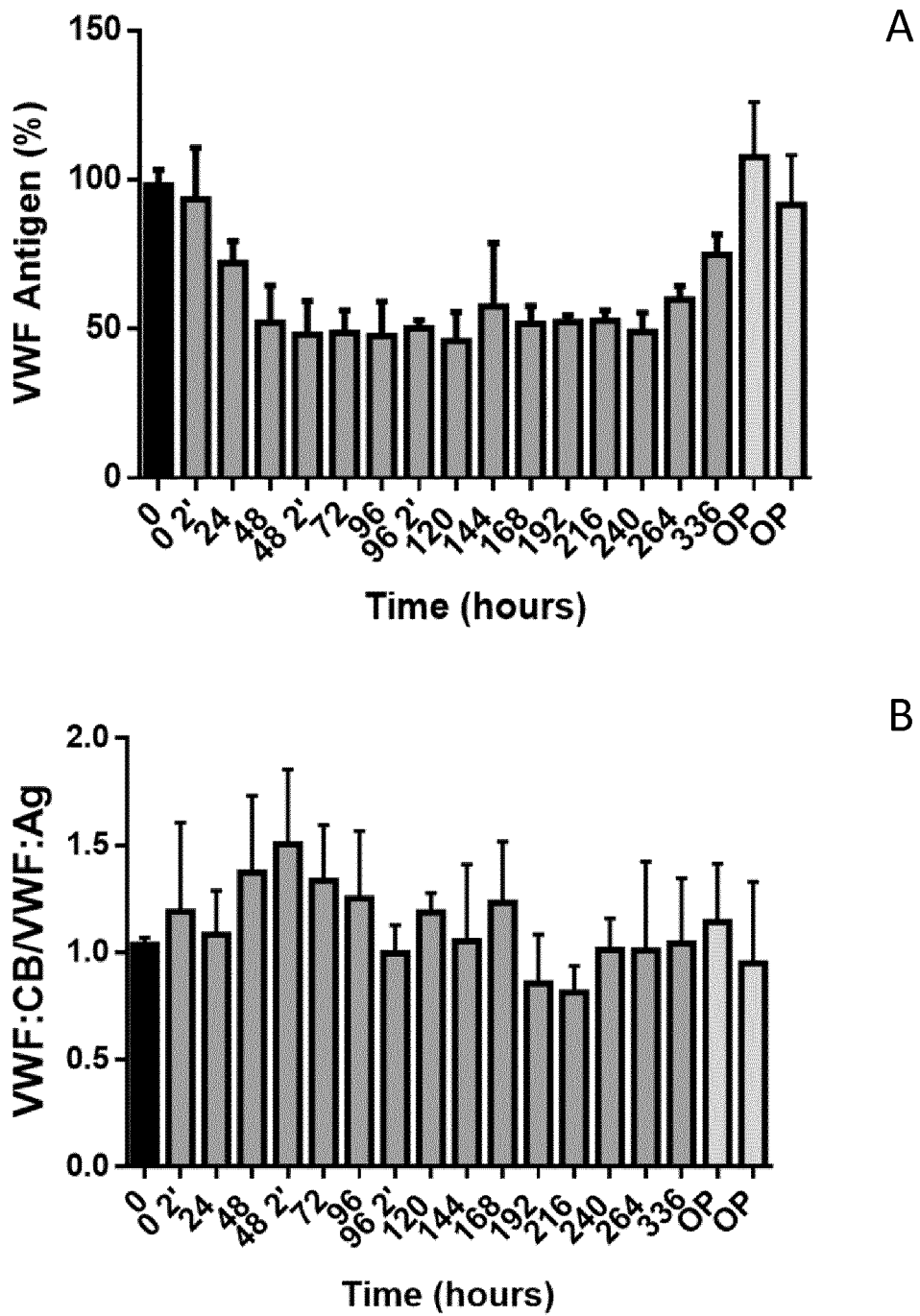
FIG. 12 shows the VWF antigen levels and VWF collagen binding activity of sheep injected with the 17C7 antibody.

A 96-well ELISA plate was coated with anti-human VWF antibodies (1/1000 dilution), ovine plasma (OP) was added and bound VWF was detected with polyclonal anti-human VWF antibodies labelled with horse radish peroxidase (HRP). Colouring reaction was performed with orthophenylene diamine (OPD) and $H_2O_2$. The reaction was stopped with $H_2SO_4$. To measure the collagen binding activity (VWF:CB), 25 μg/mL human collagen type III was coated on a 96-well ELISA plate, ovine plasma was added and bound VWF was detected with polyclonal anti-human VWF antibodies labelled with horse radish peroxidase. Colouring reaction was performed with orthophenylene diamine (OPD) and $H_2O_2$. The reaction was stopped with $H_2SO_4$. VWF antigen levels decreased (FIG. 12A) after the injection of monoclonal antibody 17C7, but VWF:CB/VWF:Ag ratios were normal (FIG. 12B).

Hematological Parameters in a Sheep After Injection of Monoclonal Anti-ADAMTS13 Antibody 17C7

Figure 13:
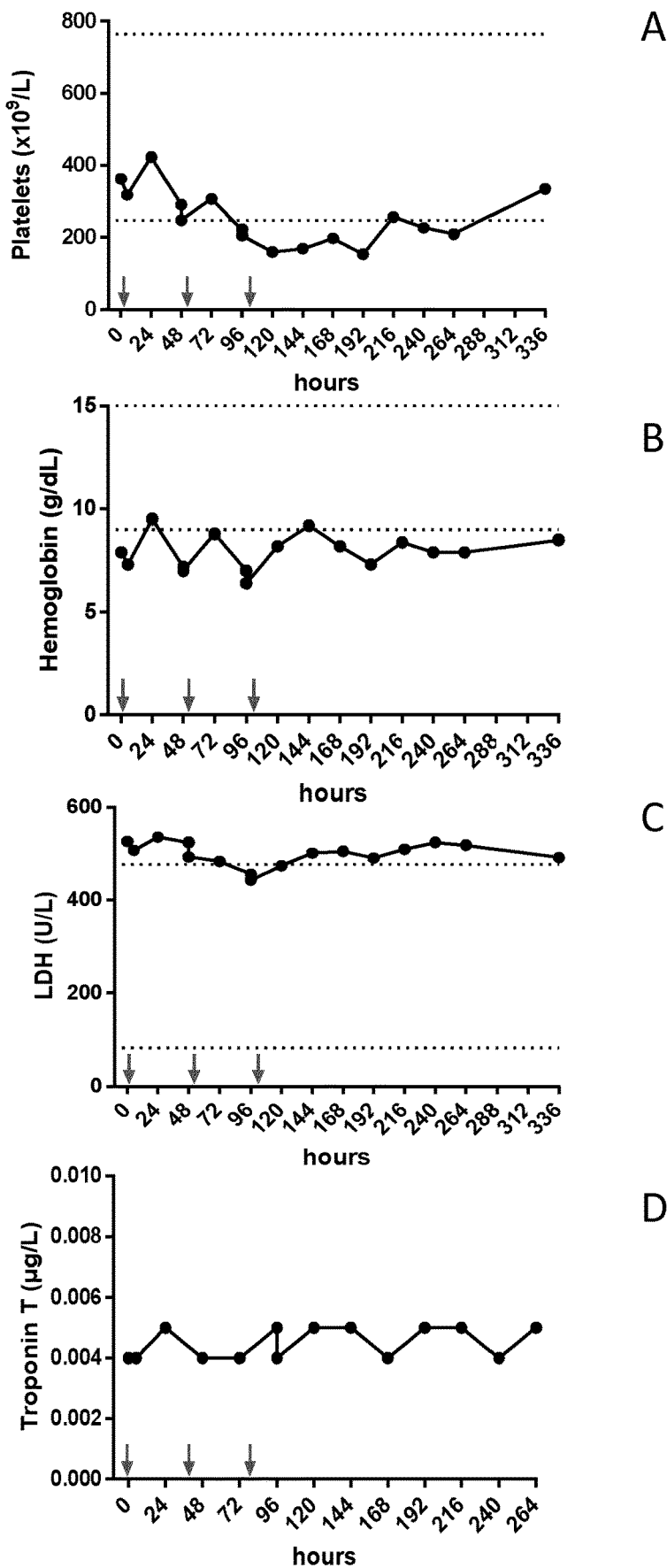
FIG. 13 shows various haematological parameters after injection with the 17C7 antibody.

Whole blood was collected to perform blood cell counts (platelets (FIG. 13A)), white blood cells (FIG. 13F) red blood cells (FIG. 13G), haemoglobin (FIG. 13B) and to measure lactate dehydrogenase (LDH) (FIG. 31C) (marker of tissue damage), tropononin T (FIG. 13D) (maker for heart failure) and creatinin (FIG. 13E) (marker for kidney failure) levels. Blood parameters were normal but the platelet count dropped from 96 hours until day 9 below reference values (dotted line) (FIG. 13A).

All experiments in examples 1 to 4 are repeated with antibodies as defined in table 1, with murine antibodies 3H9 and 17C as comparative examples.

Example 5: Generation of Humanised Antibodies of 17C7

The VH and VL sequences of the 17C7 antibody were compared to databases of human VH and VL germline sequences from the NCBI website (Ye et al. (2013) *Nucleic Acids Res.* 41, W34-W40). The databases used were IMGT human VH genes (F+ORF, 273 germline sequences) and IMGT human VLkappa genes (F+ORF, 74 germline sequences).

For 17C7 VH, human germline IGHV3-21 (allele 1) was chosen as the acceptor sequence and the human heavy chain IGHJ4 (allele 1) joining region (J gene) was chosen from human joining region sequences compiled at IMGT (international ImMunoGeneTics information system)® www.imgt.org (Lefranc et al. (2015) *Nucleic Acids Res.* 43, D413-422).

For 17C7 VL, human germline IGKV3-11 (allele 1) was chosen as the acceptor sequence and human light chain IGKJ2 (allele 1) joining region (J gene) was chosen from human joining region sequences compiled at IMGT®.

CDRs were defined according to the AbM definition. Alteration of human germline framework (i.e., non-CDR residues in VH and VL) positions to corresponding parental murine sequence might be required to optimize binding of the humanized antibody. Asn may be subject to posttranslational modifications and may be modified to Gln, Ser, Ala or Asp.

In the VH domain, Asn31 has a low potential for deamidation based on sequence and could show a low level of this post-translational modification.

In the VL domain, CDR-L1 Asn24 has a low potential for deamidation based on sequence and conformation and could show a low level of this post-translational modification.

Asn91-Gly92 in CDR-L3 is likely to be solvent-exposed and could show deamidation and isoaspartate formation, especially under stress conditions. All of the Asn residues noted in the CDRs have a low/medium propensity for deamidation/isoaspartate formation based on sequence and position.

hMAB2-L5a and -L5b are included primarily to reduce potential immunogenicity. Asn24 in CDR-L1 is unusual for both humans and mice. The Asn24 sidechain will be exposed to solvent but has a low potential to participate in binding to the target. As an alternative this residue is changed to human Arg24 and binding re-tested; if there is no effect on binding, then Arg24 can be retained.

FIG. 14 shows an alignment of the 17C sequence and humanised versions thereof.

FIG. 14 further shows the various sequence elements of C17 and its humanised versions (Frameworks, CDR regions and frameworks)

The above engineered sequences were cloned and transfected following standard cloning techniques.

Antibodies with the following combinations of VH and VL chains were generated:

TABLE 1

|  | VH |  | VL |  |
| --- | --- | --- | --- | --- |
| chMAB2 | chimVH | [SEQ ID NO: 2] | chimVL | [SEQ ID NO: 5] |
| hMAB2-1 | hMAB2-H1 | [SEQ ID NO: 3] | hMAB2-L1 | [SEQ ID NO: 7] |
| hMAB2-2 | hMAB2-H1 | [SEQ ID NO: 3] | hMAB2-L2 | [SEQ ID NO: 8] |
| hMAB2-3 | hMAB2-H1 | [SEQ ID NO: 3] | hMAB2-L3 | [SEQ ID NO: 9] |
| hMAB2-4 | hMAB2-H1 | [SEQ ID NO: 3] | hMAB2-L4 | [SEQ ID NO: 11] |
| hMAB2-5 | hMAB2-H2 | [SEQ ID NO: 4] | hMAB2-L2 | [SEQ ID NO: 8] |
| hMAB2-6 | hMAB2-H2 | [SEQ ID NO: 4] | hMAB2-L3 | [SEQ ID NO: 9] |
| hMAB2-7 | hMAB2-H2 | [SEQ ID NO: 4] | hMAB2-L4 | [SEQ ID NO: 11] |
| hMAB2-8 | hMAB2-H2 | [SEQ ID NO: 4] | hMAB2-L5a | [SEQ ID NO: 10] (hMAB2-6 derivative) |
| hMAB2-9 | hMAB2-H2 | [SEQ ID NO: 4] | hMAB2-L5b | [SEQ ID NO: 12] (hMAB2-7 derivative) |

The antibodies are secreted by the cell line and purified with affinity chromatography on Protein G. The column is equilibrated with 20 mM Tris pH 7.5, 150 mM NaCl, and washed after loading with 20 mM Tris pH 7.5, 1M NaCl. Bound antibodies are eluted with 1 M Glycine, pH 3.5.

Example 6 Characterisation of Antibodies

The purified humanised antibodies are tested for ADAMTS13 inhibition using 125 ng antibody a peptide with an ADAMTS cleavage site and comprising quenching group [Kokame et al., cited above]. Upon proteolysis of the peptide light is emitted by the chromophoric group of the peptide.

Controls are "plasma" containing ADAMTS13 (positive control), whereby the peptide is gradually degraded over time. "EDTA" is the negative control wherein EDTA is added to plasma, which inhibits Zinc metalloproteases such as ADAMTS13.

Mu17c7 is a control with the murine 17C7 AB. The nature of the various humanised Ab is shown in Table 1.

Figure 15:
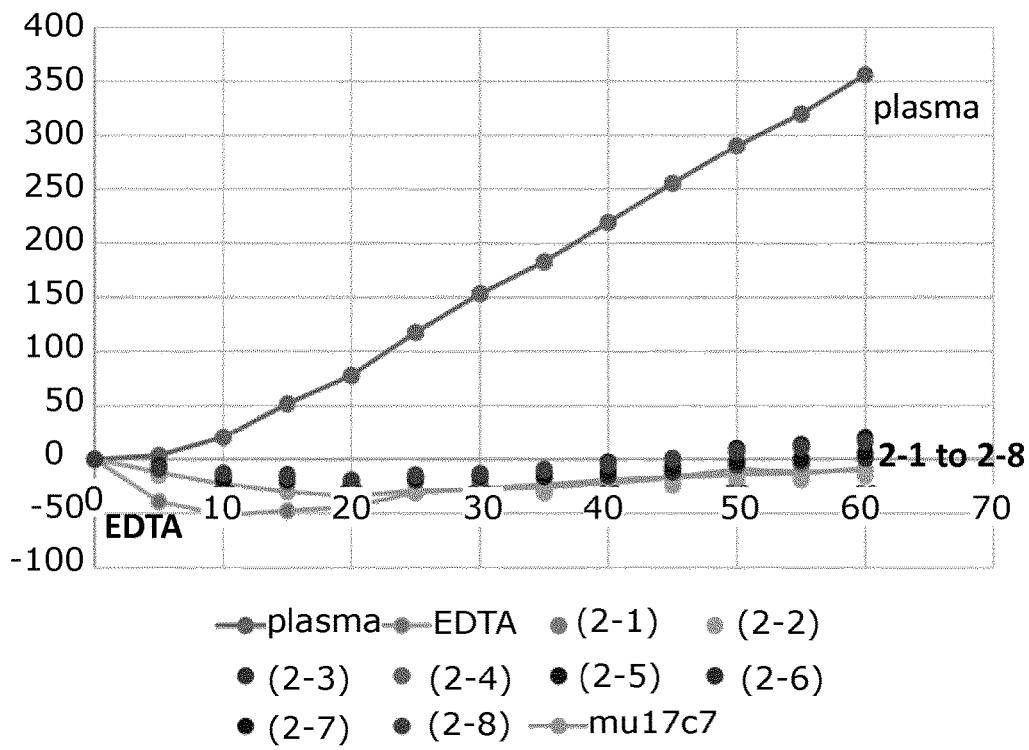
FIGS. 15 and 16 show FRET assays of humanised versions of 17C7.

FIG. 15 illustrates that at the used concentration of 125 ng, all humanised antibodies are as effective as the murine counterpart or as EDTA.

Figure 16:
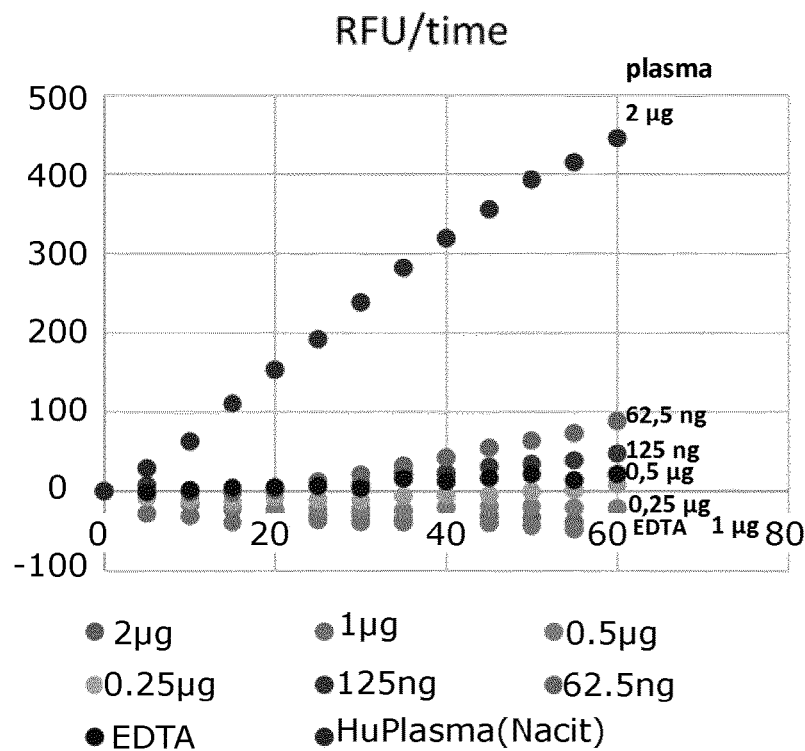

FIG. 16 illustrates the same assay for the (2-9) version of the humanised version at various concentrations. The lowest concentrations of the antibody show a dose dependent activity.

The experiment was repeated for the other humanised Ab shown in Table 1 and show the same efficacy.

The invention claimed is:

1. A humanized antibody, specifically binding to ADAMTS13 and inhibiting VWF cleavage by ADAMTS13, or an antigen binding fragment of the antibody, the humanized antibody or the antigen binding fragment of the antibody comprising:

a variable heavy (VH) chain comprising:
a Framework 1 having the sequence

EVQLVESGGGLVKPGGSLRLSCAAS; [SEQ ID NO: 14]

a CDR1 region having the sequence

GFIFSNYAMS [SEQ ID NO: 16]

a Framework 2 having the sequence

WVRQAPGKGLEWVS [SEQ ID NO: 19]
or
WVRQAPGKGLEWGA; [SEQ ID NO: 20]

a CDR2 region having the sequence

TITTGGFYTF; [SEQ ID NO: 21]

a Framework 3 having the sequence

YSDSVKGRFTISRDNAKNTLYLQMSSLRSEDTAMYYCAR [SEQ ID NO: 23]
or
YADSVKGRFTISRDNAKNSLYLQMNSLRAEDTAVYYCAR; [SEQ ID NO: 24]

a CDR3 region having the sequence

HRYDDYYALDY; [SEQ ID NO: 25]

and
a Framework 4 having the sequence

WGQGTLVTVSS; [SEQ ID NO: 27]

and
a variable light (VL) chain comprising:
a framework 1 having the sequence

EIVLTQSPATLSLSPGERATLSC, [SEQ ID NO: 30]
EIVLTQSPATLSLSPGERVTMSC, [SEQ ID NO: 31]
or
EIVLTQSPATMSTSPGERVTMSC; [SEQ ID NO: 32]

a CDR1 region having the sequence

NVSSSVSYMR [SEQ ID NO: 34]
or
RVSSSVSYMR; [SEQ ID NO: 35]

a framework 2 having the sequence

WYQQKPGQAPRLLIY [SEQ ID NO: 38]
or
WFQQKPGQAPRLWIY; [SEQ ID NO: 39]

a CDR2 region having the sequence

DTSKLAS; [SEQ ID NO: 40]

a framework 3 having the sequence

GIPARFSGSGSGTDFTLTISSLEPEDFAVYYC, [SEQ ID NO: 43]

-continued

GIPARFSGSGSGTDYTLTISSLEPEDFAVYYC, [SEQ ID NO: 44]

GVPARFSGSGSGTDYTLTISSMEPEDFAVYYC, [SEQ ID NO: 45]
or

GVPARFSGSGSGTDYTLTISSMEPEDFAVYYC; [SEQ ID NO: 46]

a CDR3 region having the sequence

FQGNGYPLT [SEQ ID NO: 48]

and
a Framework 4 having the sequence

FGQGTKLEIK. [SEQ ID NO: 51]

2. The antigen binding molecule of claim 1, wherein the antigen binding fragment is selected from the group consisting of a Fab', F(ab')2, Fab, Fv, vIgG, an scFv fragment, rIgG, a disulfide-stabilized Fv antibody (dsFv), a diabody, and triabody.

3. The antigen binding molecule of claim 1, wherein the antigen binding fragment is selected from the group consisting of a scFv, Fab, Fab2, F(ab')2, and Fv.

4. The antibody of claim 1, wherein the VH chain comprises the sequence with SEQ ID NO:3 or SEQ ID NO:4.

5. The antibody of claim 1, wherein the VL chain comprises the sequences with SEQ ID NO:6, SEQ ID NO:7, SEQ ID NO:8, SEQ ID NO:9, SEQ ID NO:10, SEQ ID NO:11, and SEQ ID NO:12.

6. A nucleic acid encoding an antibody or antigen binding fragment in accordance with claim 1.

7. A method of treatment of a haemorrhagic complication or bleeding disorder in a subject carrying an implanted circulatory assist device, the method comprising administering an antibody or antigen binding fragment according to claim 1.

\* \* \* \* \*

UNITED STATES PATENT AND TRADEMARK OFFICE
CERTIFICATE OF CORRECTION

PATENT NO. : 11,339,226 B2
APPLICATION NO. : 16/638677
DATED : May 24, 2022
INVENTOR(S) : Karen Vanhoorelbeke, Shannen F. Deconinck and An-Sofie Schelpe It is certified that error appears in the above-identified patent and that said Letters Patent is hereby corrected as shown below:

On the Title Page

Item (74), attorney, agent, or firm, after "Shohl", delete ",".
In page 2, Column 1, item (56), other publications, cite no. 9, delete "metal" and insert --metal- --, therefor.
In page 2, Column 1, item (56), other publications, cite no. 13, before "The immunogenicity", insert --"--.
In page 2, Column 1, item (56), other publications, cite no. 13, after "antibodies", insert --"--.
In page 2, Column 2, item (56), other publications, cite no. 2, delete "Melson" and insert --Nelson--, therefor.
In page 3, Column 1, item (56), other publications, cite no. 1, before "CDR Walking", insert --"--.
In page 3, Column 1, item (56), other publications, cite no. 1, after "Range", insert --"--.

In the Specification

In Column 5, Line(s) 30, after "shows", delete "the".

In the Claims

In Column 57, Line(s) 37, Claim 1, after "GFIFSNYAMS", insert --;--.
In Column 59, Line(s) 14, Claim 1, after "FQGNGYPLT", insert --;--.

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 58

<210> SEQ ID NO 1
<211> LENGTH: 120
<212> TYPE: PRT
<213> ORGANISM: artificial sequence
<220> FEATURE:
<223> OTHER INFORMATION: humanised monoclonal antibody fragment

<400> SEQUENCE: 1

```
Glu Val Gln Leu Val Glu Ser Gly Gly Asp Leu Val Lys Ser Gly Gly
1               5                   10                  15

Ser Leu Lys Leu Ser Cys Ala Ala Ser Gly Phe Ile Phe Ser Asn Tyr
                20                  25                  30

Ala Met Ser Trp Val Arg Gln Thr Pro Glu Lys Arg Leu Glu Trp Gly
            35                  40                  45

Ala Thr Ile Thr Thr Gly Gly Phe Tyr Thr Phe Tyr Ser Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Arg Tyr Asp Asp Tyr Tyr Ala Leu Asp Tyr Trp Gly Gln
            100                 105                 110
```

```
Gly Thr Ser Val Thr Val Ser Ser
        115                 120

<210> SEQ ID NO 2
<211> LENGTH: 109
<212> TYPE: PRT
<213> ORGANISM: artificial sequence
<220> FEATURE:
<223> OTHER INFORMATION: humanised monoclonal antibody fragment

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 3
<211> LENGTH: 120
<212> TYPE: PRT
<213> ORGANISM: artificial sequence
<220> FEATURE:
<223> OTHER INFORMATION: humanised monoclonal antibody fragments

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Tyr
            20                  25                  30

Ala Met Ser Trp Val Arg Gln Ala Pro Gly Lys Gly Leu Glu Trp Val
        35                  40                  45

Ser Thr Ile Thr Thr Gly Gly Phe Tyr Thr Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Tyr Asp Asp Tyr Tyr Ala Leu Asp Tyr Trp Gly Gln
            100                 105                 110

Gly Thr Leu Val Thr Val Ser Ser
        115                 120

<210> SEQ ID NO 4
<211> LENGTH: 120
<212> TYPE: PRT
<213> ORGANISM: artificial sequence
<220> FEATURE:
<223> OTHER INFORMATION: humanised monoclonal antibody fragments

<400> SEQUENCE: 4
```

```
Glu Val Gln Leu Val Glu Ser Gly Gly Leu Val Lys Pro Gly Gly
1               5                   10                  15

Ser Leu Arg Leu Ser Cys Ala Ala Ser Gly Phe Ile Phe Ser Asn Tyr
            20                  25                  30

Ala Met Ser Trp Val Arg Gln Ala Pro Gly Lys Gly Leu Glu Trp Gly
            35                  40                  45

Ala Thr Ile Thr Thr Gly Gly Phe Tyr Thr Phe Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Tyr Asp Asp Tyr Tyr Ala Leu Asp Tyr Trp Gly Gln
            100                 105                 110

Gly Thr Leu Val Thr Val Ser Ser
        115                 120
```

<210> SEQ ID NO 5
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 5

```
Glu Asn Val Leu Thr Gln Ser Pro Ala Ile Met Ser Thr Ser Pro Gly
1               5                   10                  15

Glu Lys Val Thr Met Thr Cys Asn Val Ser Ser Ser Val Ser Tyr Met
            20                  25                  30

Arg Trp Phe Gln Gln Lys Ser Thr Ser Pro Lys Leu Trp Ile Tyr
            35                  40                  45

Asp Thr Ser Lys Leu Ala Ser Gly Val Pro Gly Arg Phe Ser Gly Ser
        50                  55                  60

Gly Ser Gly His Ser Tyr Ser Leu Thr Ile Ser Ser Met Glu Ala Asp
65                  70                  75                  80

Asp Val Ala Thr Tyr Tyr Cys Phe Gln Gly Asn Gly Tyr Pro Leu Thr
                85                  90                  95

Phe Gly Ala Gly Thr Lys Leu Glu Leu Lys
            100                 105
```

<210> SEQ ID NO 6
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 6

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Pro
                85                  90                  95

Phe Gly Gln Gly Thr Lys Leu Glu Ile Lys
            100                 105

<210> SEQ ID NO 7
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Asn Val Ser Ser Ser Val Ser Tyr Met
            20                  25                  30

Arg Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Asn Gly Tyr Pro Leu Thr
                85                  90                  95

Phe Gly Gln Gly Thr Lys Leu Glu Ile Lys
            100                 105

<210> SEQ ID NO 8
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Asn Val Ser Ser Ser Val Ser Tyr Met
            20                  25                  30

Arg Trp Phe Gln Gln Lys Pro Gly Gln Ala Pro Arg Leu Trp Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Phe Gln Gly Asn Gly Tyr Pro Leu Thr
                85                  90                  95

Phe Gly Gln Gly Thr Lys Leu Glu Ile Lys
            100                 105

<210> SEQ ID NO 9
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 9

Glu Ile Val Leu Thr Gln Ser Pro Ala Thr Leu Ser Leu Ser Pro Gly
1               5                   10                  15

Glu Arg Val Thr Met Ser Cys Asn Val Ser Ser Val Ser Tyr Met
            20                  25                  30

Arg Trp Phe Gln Gln Lys Pro Gly Gln Ala Pro Arg Leu Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Phe Gln Gly Asn Gly Tyr Pro Leu Thr
                85                  90                  95

Phe Gly Gln Gly Thr Lys Leu Glu Ile Lys
            100                 105

<210> SEQ ID NO 10
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 10

Glu Ile Val Leu Thr Gln Ser Pro Ala Thr Leu Ser Leu Ser Pro Gly
1               5                   10                  15

Glu Arg Val Thr Met Ser Cys Arg Val Ser Ser Val Ser Tyr Met
            20                  25                  30

Arg Trp Phe Gln Gln Lys Pro Gly Gln Ala Pro Arg Leu Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Phe Gln Gly Asn Gly Tyr Pro Leu Thr
                85                  90                  95

Phe Gly Gln Gly Thr Lys Leu Glu Ile Lys
            100                 105

<210> SEQ ID NO 11
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 11

Glu Ile Val Leu Thr Gln Ser Pro Ala Thr Met Ser Thr Ser Pro Gly
1               5                   10                  15

Glu Arg Val Thr Met Ser Cys Asn Val Ser Ser Val Ser Tyr Met
            20                  25                  30

Arg Trp Phe Gln Gln Lys Pro Gly Gln Ala Pro Arg Leu Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Phe Gln Gly Asn Gly Tyr Pro Leu Thr
                85                  90                  95

```
Phe Gly Gln Gly Thr Lys Leu Glu Ile Lys
            100                 105

<210> SEQ ID NO 12
<211> LENGTH: 106
<212> TYPE: PRT
<213> ORGANISM: artificial sequence
<220> FEATURE:
<223> OTHER INFORMATION: humanised monoclonal antibody fragments

<400> SEQUENCE: 12

Glu Ile Val Leu Thr Gln Ser Pro Ala Thr Met Ser Thr Ser Pro Gly
1               5                   10                  15

Glu Arg Val Thr Met Ser Cys Arg Val Ser Ser Ser Val Ser Tyr Met
            20                  25                  30

Arg Trp Phe Gln Gln Lys Pro Gly Gln Ala Pro Arg Leu Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Phe Gln Gly Asn Gly Tyr Pro Leu Thr
                85                  90                  95

Phe Gly Gln Gly Thr Lys Leu Glu Ile Lys
            100                 105

<210> SEQ ID NO 13
<211> LENGTH: 25
<212> TYPE: PRT
<213> ORGANISM: artificial sequence
<220> FEATURE:
<223> OTHER INFORMATION: humanised monoclonal antibody fragments

<400> SEQUENCE: 13

Glu Val Gln Leu Val Glu Ser Gly Gly Asp Leu Val Lys Ser Gly Gly
1               5                   10                  15

Ser Leu Lys Leu Ser Cys Ala Ala Ser
            20                  25

<210> SEQ ID NO 14
<211> LENGTH: 25
<212> TYPE: PRT
<213> ORGANISM: artificial sequence
<220> FEATURE:
<223> OTHER INFORMATION: humanised monoclonal antibody fragments

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 15
<211> LENGTH: 10
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (6)..(6)
<223> OTHER INFORMATION: Xaa can be Asn, Gln, Ser, Ala or Asp
```

```
<400> SEQUENCE: 15

Gly Phe Ile Phe Ser Xaa Tyr Ala Met Ser
1               5                   10

<210> SEQ ID NO 16
<211> LENGTH: 10
<212> TYPE: PRT
<213> ORGANISM: artificial sequence
<220> FEATURE:
<223> OTHER INFORMATION: humanised monoclonal antibody fragments

<400> SEQUENCE: 16

Gly Phe Ile Phe Ser Asn Tyr Ala Met Ser
1               5                   10

<210> SEQ ID NO 17
<211> LENGTH: 14
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (13)..(13)
<223> OTHER INFORMATION: Xaa is Val or Gly
<220> FEATURE:
<221> NAME/KEY: MISC_FEATURE
<222> LOCATION: (14)..(14)
<223> OTHER INFORMATION: Xaa is Ser or Ala

<400> SEQUENCE: 17

Trp Val Arg Gln Ala Pro Gly Lys Gly Leu Glu Trp Xaa Xaa
1               5                   10

<210> SEQ ID NO 18
<211> LENGTH: 14
<212> TYPE: PRT
<213> ORGANISM: artificial sequence
<220> FEATURE:
<223> OTHER INFORMATION: humanised monoclonal antibody fragments

<400> SEQUENCE: 18

Trp Val Arg Gln Thr Pro Glu Lys Arg Leu Glu Trp Gly Ala
1               5                   10

<210> SEQ ID NO 19
<211> LENGTH: 14
<212> TYPE: PRT
<213> ORGANISM: artificial sequence
<220> FEATURE:
<223> OTHER INFORMATION: humanised monoclonal antibody fragments

<400> SEQUENCE: 19

Trp Val Arg Gln Ala Pro Gly Lys Gly Leu Glu Trp Val Ser
1               5                   10

<210> SEQ ID NO 20
<211> LENGTH: 14
<212> TYPE: PRT
<213> ORGANISM: artificial sequence
<220> FEATURE:
<223> OTHER INFORMATION: humanised monoclonal antibody fragments

<400> SEQUENCE: 20

Trp Val Arg Gln Ala Pro Gly Lys Gly Leu Glu Trp Gly Ala
1               5                   10
```

-continued

```
<210> SEQ ID NO 21
<211> LENGTH: 10
<212> TYPE: PRT
<213> ORGANISM: artificial sequence
<220> FEATURE:
<223> OTHER INFORMATION: humanised monoclonal antibody fragments

<400> SEQUENCE: 21

Thr Ile Thr Thr Gly Gly Phe Tyr Thr Phe
1               5                   10

<210> SEQ ID NO 22
<211> LENGTH: 39
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (2)..(2)
<223> OTHER INFORMATION: Xaa is Ala or Ser
<220> FEATURE:
<221> NAME/KEY: MISC_FEATURE
<222> LOCATION: (34)..(34)
<223> OTHER INFORMATION: Xaa is Met or Val

<400> SEQUENCE: 22

Tyr Xaa Asp Ser Val Lys Gly Arg Phe Thr Ile Ser Arg Asp Asn Ala
1               5                   10                  15

Lys Asn Ser Leu Tyr Leu Gln Met Asn Ser Leu Arg Ala Glu Asp Thr
            20                  25                  30

Ala Xaa Tyr Tyr Cys Ala Arg
        35

<210> SEQ ID NO 23
<211> LENGTH: 39
<212> TYPE: PRT
<213> ORGANISM: artificial sequence
<220> FEATURE:
<223> OTHER INFORMATION: humanised monoclonal antibody fragments

<400> SEQUENCE: 23

Tyr Ser Asp Ser Val Lys Gly Arg Phe Thr Ile Ser Arg Asp Asn Ala
1               5                   10                  15

Lys Asn Thr Leu Tyr Leu Gln Met Ser Ser Leu Arg Ser Glu Asp Thr
            20                  25                  30

Ala Met Tyr Tyr Cys Ala Arg
        35

<210> SEQ ID NO 24
<211> LENGTH: 39
<212> TYPE: PRT
<213> ORGANISM: artificial sequence
<220> FEATURE:
<223> OTHER INFORMATION: humanised monoclonal antibody fragments

<400> SEQUENCE: 24

Tyr Ala Asp Ser Val Lys Gly Arg Phe Thr Ile Ser Arg Asp Asn Ala
1               5                   10                  15

Lys Asn Ser Leu Tyr Leu Gln Met Asn Ser Leu Arg Ala Glu Asp Thr
            20                  25                  30

Ala Val Tyr Tyr Cys Ala Arg
        35

<210> SEQ ID NO 25
```

```
<211> LENGTH: 11
<212> TYPE: PRT
<213> ORGANISM: artificial sequence
<220> FEATURE:
<223> OTHER INFORMATION: humanised monoclonal antibody fragments

<400> SEQUENCE: 25

His Arg Tyr Asp Asp Tyr Tyr Ala Leu Asp Tyr
1               5                   10

<210> SEQ ID NO 26
<211> LENGTH: 11
<212> TYPE: PRT
<213> ORGANISM: artificial sequence
<220> FEATURE:
<223> OTHER INFORMATION: humanised monoclonal antibody fragments

<400> SEQUENCE: 26

Trp Gly Gln Gly Thr Ser Val Thr Val Ser Ser
1               5                   10

<210> SEQ ID NO 27
<211> LENGTH: 11
<212> TYPE: PRT
<213> ORGANISM: artificial sequence
<220> FEATURE:
<223> OTHER INFORMATION: humanised monoclonal antibody fragments

<400> SEQUENCE: 27

Trp Gly Gln Gly Thr Leu Val Thr Val Ser Ser
1               5                   10

<210> SEQ ID NO 28
<211> LENGTH: 23
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (2)..(2)
<223> OTHER INFORMATION: Xaa is Ile or Asn
<220> FEATURE:
<221> NAME/KEY: MISC_FEATURE
<222> LOCATION: (11)..(11)
<223> OTHER INFORMATION: Xaa is Leu or Met
<220> FEATURE:
<221> NAME/KEY: MISC_FEATURE
<222> LOCATION: (13)..(13)
<223> OTHER INFORMATION: Xaa is Leu or Thr
<220> FEATURE:
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (21)..(21)
<223> OTHER INFORMATION: Xaa is Leu or Met

<400> SEQUENCE: 28

Glu Xaa Val Leu Thr Gln Ser Pro Ala Thr Xaa Ser Xaa Ser Pro Gly
1               5                   10                  15

Glu Arg Xaa Thr Xaa Ser Cys
                20

<210> SEQ ID NO 29
<211> LENGTH: 23
<212> TYPE: PRT
<213> ORGANISM: artificial sequence
<220> FEATURE:
```

<223> OTHER INFORMATION: humanised monoclonal antibody fragments

<400> SEQUENCE: 29

Glu Asn Val Leu Thr Gln Ser Pro Ala Ile Met Ser Thr Ser Pro Gly
1               5                   10                  15

Glu Lys Val Thr Met Thr Cys
            20

<210> SEQ ID NO 30
<211> LENGTH: 23
<212> TYPE: PRT
<213> ORGANISM: artificial sequence
<220> FEATURE:
<223> OTHER INFORMATION: humanised monoclonal antibody fragments

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 31
<211> LENGTH: 23
<212> TYPE: PRT
<213> ORGANISM: artificial sequence
<220> FEATURE:
<223> OTHER INFORMATION: humanised monoclonal antibody fragments

<400> SEQUENCE: 31

Glu Ile Val Leu Thr Gln Ser Pro Ala Thr Leu Ser Leu Ser Pro Gly
1               5                   10                  15

Glu Arg Val Thr Met Ser Cys
            20

<210> SEQ ID NO 32
<211> LENGTH: 23
<212> TYPE: PRT
<213> ORGANISM: artificial sequence
<220> FEATURE:
<223> OTHER INFORMATION: humanised monoclonal antibody fragments

<400> SEQUENCE: 32

Glu Ile Val Leu Thr Gln Ser Pro Ala Thr Met Ser Thr Ser Pro Gly
1               5                   10                  15

Glu Arg Val Thr Met Ser Cys
            20

<210> SEQ ID NO 33
<211> LENGTH: 10
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (1)..(1)
<223> OTHER INFORMATION: Xaa can be Arg, Asn, Gln, Ser, Ala or Asp

<400> SEQUENCE: 33

Xaa Val Ser Ser Ser Val Ser Tyr Met Arg
1               5                   10

<210> SEQ ID NO 34
<211> LENGTH: 10
<212> TYPE: PRT

```
<213> ORGANISM: artificial sequence
<220> FEATURE:
<223> OTHER INFORMATION: humanised monoclonal antibody fragments

<400> SEQUENCE: 34

Asn Val Ser Ser Ser Val Ser Tyr Met Arg
1               5                   10

<210> SEQ ID NO 35
<211> LENGTH: 10
<212> TYPE: PRT
<213> ORGANISM: artificial sequence
<220> FEATURE:
<223> OTHER INFORMATION: humanised monoclonal antibody fragments

<400> SEQUENCE: 35

Arg Val Ser Ser Ser Val Ser Tyr Met Arg
1               5                   10

<210> SEQ ID NO 36
<211> LENGTH: 15
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (2)..(2)
<223> OTHER INFORMATION: Xaa is Tyr or Phe
<220> FEATURE:
<221> NAME/KEY: MISC_FEATURE
<222> LOCATION: (9)..(9)
<223> OTHER INFORMATION: Xaa is Ala or Ser
<220> FEATURE:
<221> NAME/KEY: MISC_FEATURE
<222> LOCATION: (13)..(13)
<223> OTHER INFORMATION: Xaa is Leu or Trp

<400> SEQUENCE: 36

Trp Xaa Gln Gln Lys Pro Gly Gln Xaa Pro Arg Leu Xaa Ile Tyr
1               5                   10                  15

<210> SEQ ID NO 37
<211> LENGTH: 15
<212> TYPE: PRT
<213> ORGANISM: artificial sequence
<220> FEATURE:
<223> OTHER INFORMATION: humanised monoclonal antibody fragments

<400> SEQUENCE: 37

Trp Phe Gln Gln Lys Ser Ser Thr Ser Pro Lys Leu Trp Ile Tyr
1               5                   10                  15

<210> SEQ ID NO 38
<211> LENGTH: 15
<212> TYPE: PRT
<213> ORGANISM: artificial sequence
<220> FEATURE:
<223> OTHER INFORMATION: humanised monoclonal antibody fragments

<400> SEQUENCE: 38

Trp Tyr Gln Gln Lys Pro Gly Gln Ala Pro Arg Leu Leu Ile Tyr
1               5                   10                  15

<210> SEQ ID NO 39
<211> LENGTH: 15
<212> TYPE: PRT
<213> ORGANISM: artificial sequence
<220> FEATURE:
```

<223> OTHER INFORMATION: humanised monoclonal antibody fragments

<400> SEQUENCE: 39

Trp Phe Gln Gln Lys Pro Gly Gln Ala Pro Arg Leu Trp Ile Tyr
1               5                   10                  15

<210> SEQ ID NO 40
<211> LENGTH: 7
<212> TYPE: PRT
<213> ORGANISM: artificial sequence
<220> FEATURE:
<223> OTHER INFORMATION: humanised monoclonal antibody fragments

<400> SEQUENCE: 40

Asp Thr Ser Lys Leu Ala Ser
1               5

<210> SEQ ID NO 41
<211> LENGTH: 32
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (2)..(2)
<223> OTHER INFORMATION: Xaa is Ile or Val
<220> FEATURE:
<221> NAME/KEY: MISC_FEATURE
<222> LOCATION: (15)..(15)
<223> OTHER INFORMATION: Xaa is Tyr or Phe
<220> FEATURE:
<221> NAME/KEY: MISC_FEATURE
<222> LOCATION: (22)..(22)
<223> OTHER INFORMATION: Xaa is Leu or Met
<220> FEATURE:
<221> NAME/KEY: MISC_FEATURE
<222> LOCATION: (27)..(27)
<223> OTHER INFORMATION: Xaa is Phe or Val

<400> SEQUENCE: 41

Gly Xaa Pro Ala Arg Phe Ser Gly Ser Gly Ser Gly Thr Asp Xaa Thr
1               5                   10                  15

Leu Thr Ile Ser Ser Xaa Glu Pro Glu Asp Xaa Ala Val Tyr Tyr Cys
            20                  25                  30

<210> SEQ ID NO 42
<211> LENGTH: 32
<212> TYPE: PRT
<213> ORGANISM: artificial sequence
<220> FEATURE:
<223> OTHER INFORMATION: humanised monoclonal antibody fragments

<400> SEQUENCE: 42

Gly Val Pro Gly Arg Phe Ser Gly Ser Gly Ser Gly His Ser Tyr Ser
1               5                   10                  15

Leu Thr Ile Ser Ser Met Glu Ala Asp Asp Val Ala Thr Tyr Tyr Cys
            20                  25                  30

<210> SEQ ID NO 43
<211> LENGTH: 32
<212> TYPE: PRT
<213> ORGANISM: artificial sequence
<220> FEATURE:
<223> OTHER INFORMATION: humanised monoclonal antibody fragments

<400> SEQUENCE: 43

Gly Ile Pro Ala Arg Phe Ser Gly Ser Gly Ser Gly Thr Asp Phe Thr

```
                1               5                   10                  15
Leu Thr Ile Ser Ser Leu Glu Pro Glu Asp Phe Ala Val Tyr Tyr Cys
            20                  25                  30

<210> SEQ ID NO 44
<211> LENGTH: 32
<212> TYPE: PRT
<213> ORGANISM: artificial sequence
<220> FEATURE:
<223> OTHER INFORMATION: humanised monoclonal antibody fragments

<400> SEQUENCE: 44

Gly Ile Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30

<210> SEQ ID NO 45
<211> LENGTH: 32
<212> TYPE: PRT
<213> ORGANISM: artificial sequence
<220> FEATURE:
<223> OTHER INFORMATION: humanised monoclonal antibody fragments

<400> SEQUENCE: 45

Gly Val Pro Ala Arg Phe Ser Gly Ser Gly Ser Gly Thr Asp Tyr Thr
1               5                   10                  15

Leu Thr Ile Ser Ser Met Glu Pro Glu Asp Phe Ala Val Tyr Tyr Cys
            20                  25                  30

<210> SEQ ID NO 46
<211> LENGTH: 32
<212> TYPE: PRT
<213> ORGANISM: artificial sequence
<220> FEATURE:
<223> OTHER INFORMATION: humanised monoclonal antibody fragments

<400> SEQUENCE: 46

Gly Val Pro Ala Arg Phe Ser Gly Ser Gly Ser Gly Thr Asp Tyr Thr
1               5                   10                  15

Leu Thr Ile Ser Ser Met Glu Pro Glu Asp Phe Ala Val Tyr Tyr Cys
            20                  25                  30

<210> SEQ ID NO 47
<211> LENGTH: 9
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (4)..(4)
<223> OTHER INFORMATION: Xaa is Asn, Gln, Ser or Ala

<400> SEQUENCE: 47

Phe Gln Gly Xaa Gly Tyr Pro Leu Thr
1               5

<210> SEQ ID NO 48
<211> LENGTH: 9
<212> TYPE: PRT
<213> ORGANISM: artificial sequence
<220> FEATURE:
<223> OTHER INFORMATION: humanised monoclonal antibody fragments

<400> SEQUENCE: 48
```

```
Phe Gln Gly Asn Gly Tyr Pro Leu Thr
1               5

<210> SEQ ID NO 49
<211> LENGTH: 10
<212> TYPE: PRT
<213> ORGANISM: artificial sequence
<220> FEATURE:
<223> OTHER INFORMATION: humanised monoclonal antibody fragments
<220> FEATURE:
<221> NAME/KEY: MISC_FEATURE
<222> LOCATION: (9)..(9)
<223> OTHER INFORMATION: Xaa is Ile or Leu

<400> SEQUENCE: 49

Phe Gly Gln Gly Thr Lys Leu Glu Xaa Lys
1               5                   10

<210> SEQ ID NO 50
<211> LENGTH: 10
<212> TYPE: PRT
<213> ORGANISM: artificial sequence
<220> FEATURE:
<223> OTHER INFORMATION: humanised monoclonal antibody fragments

<400> SEQUENCE: 50

Phe Gly Ala Gly Thr Lys Leu Glu Leu Lys
1               5                   10

<210> SEQ ID NO 51
<211> LENGTH: 10
<212> TYPE: PRT
<213> ORGANISM: artificial sequence
<220> FEATURE:
<223> OTHER INFORMATION: humanised monoclonal antibody fragments

<400> SEQUENCE: 51

Phe Gly Gln Gly Thr Lys Leu Glu Ile Lys
1               5                   10

<210> SEQ ID NO 52
<211> LENGTH: 122
<212> TYPE: PRT
<213> ORGANISM: artificial sequence
<220> FEATURE:
<223> OTHER INFORMATION: humanised monoclonal antibody fragments

<400> SEQUENCE: 52

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Ala Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Thr Ser Glu Asp Ser Ala Met Phe Tyr Cys
                85                  90                  95

Ala Arg Arg Val Ala Trp Asp Phe Gly Ser Thr Tyr Asp Tyr Ala Met
            100                 105                 110

Asp Tyr Trp Gly Gln Gly Thr Thr Val Thr
```

```
                    115                 120
```

<210> SEQ ID NO 53
<211> LENGTH: 8
<212> TYPE: PRT
<213> ORGANISM: artificial sequence
<220> FEATURE:
<223> OTHER INFORMATION: humanised monoclonal antibody fragments

<400> SEQUENCE: 53

```
Gly Phe Thr Phe Ser Ser Tyr Gly
1               5
```

<210> SEQ ID NO 54
<211> LENGTH: 8
<212> TYPE: PRT
<213> ORGANISM: artificial sequence
<220> FEATURE:
<223> OTHER INFORMATION: humanised monoclonal antibody fragments

<400> SEQUENCE: 54

```
Ile Ser Ser Gly Gly Thr Tyr Thr
1               5
```

<210> SEQ ID NO 55
<211> LENGTH: 18
<212> TYPE: PRT
<213> ORGANISM: artificial sequence
<220> FEATURE:
<223> OTHER INFORMATION: humanised monoclonal antibody fragments

<400> SEQUENCE: 55

```
Ala Arg Arg Val Ala Trp Asp Phe Gly Ser Thr Tyr Asp Tyr Ala Met
1               5                   10                  15

Asp Tyr
```

<210> SEQ ID NO 56
<211> LENGTH: 104
<212> TYPE: PRT
<213> ORGANISM: artificial sequence
<220> FEATURE:
<223> OTHER INFORMATION: humanised monoclonal antibody fragments

<400> SEQUENCE: 56

```
Asp Ile Glu Leu Thr Gln Ser Pro Ala Thr Leu Ser Val Thr Pro Gly
1               5                   10                  15

Asp Arg Val Gly Leu Ser Cys Arg Ala Ser Gln Ser Leu Ser Asn Tyr
            20                  25                  30

Leu His Trp Tyr Gln Gln Lys Ser His Glu Ser Pro Arg Leu Leu Ile
        35                  40                  45

Asn Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Cys Phe Cys Gln Gln Ser Asn Ser Trp Pro Leu
                85                  90                  95

Thr Phe Gly Ala Gly Thr Lys Leu
            100
```

<210> SEQ ID NO 57
<211> LENGTH: 6
<212> TYPE: PRT
<213> ORGANISM: artificial sequence
<220> FEATURE:
<223> OTHER INFORMATION: humanised monoclonal antibody fragments

<400> SEQUENCE: 57

Gln Ser Leu Ser Asn Tyr
1               5

<210> SEQ ID NO 58
<211> LENGTH: 9
<212> TYPE: PRT
<213> ORGANISM: artificial sequence
<220> FEATURE:
<223> OTHER INFORMATION: humanised monoclonal antibody fragments

<400> SEQUENCE: 58

Gln Gln Ser Asn Ser Trp Pro Leu Thr
1               5